(12) United States Patent
Jaskela et al.

(10) Patent No.: US 10,430,554 B2
(45) Date of Patent: *Oct. 1, 2019

(54) MEDICATION PREPARATION QUEUE

(71) Applicant: CareFusion 303, Inc., San Diego, CA (US)

(72) Inventors: Maria Consolacion Jaskela, San Rafael, CA (US); William Lee Webster, Rockwall, TX (US); Thomas William Utech, Dallas, TX (US); Timothy W. Vanderveen, Poway, CA (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/901,501

(22) Filed: May 23, 2013

(65) Prior Publication Data
US 2014/0350950 A1  Nov. 27, 2014

(51) Int. Cl.
  *G06F 19/00* (2018.01)
  *G16H 20/10* (2018.01)
(52) U.S. Cl.
  CPC ......... *G06F 19/3456* (2013.01); *G16H 20/10* (2018.01); *Y02A 90/22* (2018.01); *Y02A 90/26* (2018.01)
(58) Field of Classification Search
  CPC ..... G06Q 50/22–50/24; G06F 19/3456; G16H 20/10
  See application file for complete search history.

(56) References Cited

U.S. PATENT DOCUMENTS

| 2,141,006 A | 12/1938 | Marinsky |
| 3,724,455 A | 4/1973 | Unger |
| 3,831,006 A | 8/1974 | Chaffin, III et al. |

(Continued)

FOREIGN PATENT DOCUMENTS

| CA | 2472098 A1 | 7/2003 |
| CA | 2554903 A1 | 4/2005 |

(Continued)

OTHER PUBLICATIONS

International Search Report and Written Opinion in PCT Patent Application No. PCT/US2014/039228 dated Aug. 22, 2014, 11 pgs.

(Continued)

*Primary Examiner* — Sheetal R Paulson
(74) *Attorney, Agent, or Firm* — Morgan, Lewis & Bockius LLP

(57) ABSTRACT

Methods for managing preparation of a medication for a patient are provided. In one aspect, a method includes receiving information indicative of an order for medication for a patient from an electronic data feed, and determining whether the order for medication for the patient can be filled with a returned medication. The method also includes providing a notification to fill the order with the returned medication when the determination indicates the order can be filled with a returned medication, and providing a notification to fill the order by preparing the medication when the determination indicates a returned medication is not available to fill the order. Systems and machine-readable media are also provided.

21 Claims, 8 Drawing Sheets

(56) References Cited

U.S. PATENT DOCUMENTS

| | | |
|---|---|---|
| 3,848,112 A | 11/1974 | Weichselbaum et al. |
| 3,872,448 A | 3/1975 | Mitchell, Jr. |
| 3,898,984 A | 8/1975 | Mandel et al. |
| 3,910,260 A | 10/1975 | Sarnoff et al. |
| 3,921,196 A | 11/1975 | Patterson |
| 3,970,996 A | 7/1976 | Yasaka et al. |
| 4,051,522 A | 9/1977 | Healy et al. |
| 4,135,241 A | 1/1979 | Stanis et al. |
| 4,164,320 A | 8/1979 | Irazoqui et al. |
| 4,216,462 A | 8/1980 | McGrath et al. |
| 4,237,344 A | 12/1980 | Moore |
| 4,315,309 A | 2/1982 | Coli |
| 4,321,461 A | 3/1982 | Walter, Jr. et al. |
| 4,360,125 A | 11/1982 | Martindale et al. |
| 4,373,527 A | 2/1983 | Fischell |
| 4,476,381 A | 10/1984 | Rubin |
| 4,604,847 A | 8/1986 | Moulding, Jr. et al. |
| 4,636,950 A | 1/1987 | Caswell et al. |
| 4,674,652 A | 6/1987 | Aten et al. |
| 4,676,776 A | 6/1987 | Howson |
| 4,688,026 A | 8/1987 | Scribner et al. |
| 4,695,954 A | 9/1987 | Rose et al. |
| 4,696,671 A | 9/1987 | Epstein et al. |
| 4,731,726 A | 3/1988 | Allen |
| 4,733,364 A | 3/1988 | Yamagata |
| 4,741,732 A | 5/1988 | Crankshaw et al. |
| 4,756,706 A | 7/1988 | Kerns et al. |
| 4,778,449 A | 10/1988 | Weber et al. |
| 4,785,969 A | 11/1988 | McLaughlin |
| 4,803,625 A | 2/1989 | Fu et al. |
| 4,810,243 A | 3/1989 | Howson |
| 4,828,545 A | 5/1989 | Epstein et al. |
| 4,831,562 A | 5/1989 | McIntosh et al. |
| 4,835,372 A | 5/1989 | Gombrich et al. |
| 4,839,806 A | 6/1989 | Goldfischer et al. |
| 4,847,764 A | 7/1989 | Halvorson |
| 4,850,009 A | 7/1989 | Zook et al. |
| 4,853,521 A | 8/1989 | Claeys et al. |
| 4,855,909 A | 8/1989 | Vincent et al. |
| 4,857,713 A | 8/1989 | Brown |
| 4,857,716 A | 8/1989 | Gombrich et al. |
| 4,865,584 A | 9/1989 | Epstein et al. |
| 4,882,575 A | 11/1989 | Kawahara |
| 4,899,839 A | 2/1990 | Dessertine et al. |
| 4,916,441 A | 4/1990 | Gombrich et al. |
| 4,918,604 A | 4/1990 | Baum |
| 4,925,444 A | 5/1990 | Orkin et al. |
| 4,942,544 A | 7/1990 | McIntosh et al. |
| 4,950,246 A | 8/1990 | Muller |
| 4,967,928 A | 11/1990 | Carter |
| 4,970,669 A | 11/1990 | McIntosh et al. |
| 4,978,335 A | 12/1990 | Arthur, III |
| 5,001,630 A | 3/1991 | Wiltfong |
| 5,006,699 A | 4/1991 | Felkener et al. |
| 5,036,462 A | 7/1991 | Kaufman et al. |
| 5,036,852 A | 8/1991 | Leishman |
| 5,041,086 A | 8/1991 | Koenig et al. |
| 5,072,383 A | 12/1991 | Brimm et al. |
| 5,077,666 A | 12/1991 | Brimm et al. |
| 5,078,683 A | 1/1992 | Sancoff et al. |
| 5,088,056 A | 2/1992 | McIntosh et al. |
| 5,088,981 A | 2/1992 | Howson et al. |
| 5,100,380 A | 3/1992 | Epstein et al. |
| 5,126,957 A | 6/1992 | Kaufman et al. |
| 5,142,484 A | 8/1992 | Kaufman et al. |
| 5,153,416 A | 10/1992 | Neeley |
| 5,153,827 A | 10/1992 | Coutre et al. |
| 5,164,575 A | 11/1992 | Neeley et al. |
| 5,166,498 A | 11/1992 | Neeley |
| 5,171,977 A | 12/1992 | Morrison |
| 5,181,910 A | 1/1993 | Scanlon |
| 5,190,522 A | 3/1993 | Wojcicki et al. |
| 5,207,642 A | 5/1993 | Orkin et al. |
| 5,235,507 A | 8/1993 | Sackler et al. |
| 5,256,157 A | 10/1993 | Samiotes et al. |
| 5,258,906 A | 11/1993 | Kroll et al. |
| 5,265,010 A | 11/1993 | Evans-Paganelli et al. |
| 5,267,174 A | 11/1993 | Kaufman et al. |
| 5,291,399 A | 3/1994 | Chaco |
| 5,292,029 A | 3/1994 | Pearson |
| 5,307,263 A | 4/1994 | Brown |
| 5,312,334 A | 5/1994 | Hara et al. |
| 5,314,243 A | 5/1994 | McDonald et al. |
| 5,315,505 A | 5/1994 | Pratt et al. |
| 5,317,506 A | 5/1994 | Coutre et al. |
| H1324 H | 6/1994 | Dalke et al. |
| 5,331,547 A | 7/1994 | Laszlo |
| 5,356,378 A | 10/1994 | Doan |
| 5,367,555 A | 11/1994 | Isoyama |
| 5,368,554 A | 11/1994 | Nazarian et al. |
| 5,371,692 A | 12/1994 | Draeger et al. |
| 5,374,813 A | 12/1994 | Shipp |
| 5,376,070 A | 12/1994 | Purvis et al. |
| 5,378,231 A | 1/1995 | Johnson et al. |
| 5,382,232 A | 1/1995 | Hague et al. |
| 5,390,238 A | 2/1995 | Kirk |
| 5,401,059 A | 3/1995 | Ferrario |
| 5,404,384 A | 4/1995 | Colburn et al. |
| 5,408,443 A | 4/1995 | Weinberger |
| 5,412,372 A | 5/1995 | Parkhurst et al. |
| 5,412,564 A | 5/1995 | Ecer |
| 5,416,695 A | 5/1995 | Stutman et al. |
| 5,456,691 A | 10/1995 | Snell |
| 5,460,605 A | 10/1995 | Tuttle et al. |
| 5,465,082 A | 11/1995 | Chaco |
| 5,472,614 A | 12/1995 | Rossi |
| 5,502,944 A | 4/1996 | Kraft et al. |
| 5,515,426 A | 5/1996 | Yacenda et al. |
| 5,522,798 A | 6/1996 | Johnson et al. |
| 5,533,079 A | 7/1996 | Colburn et al. |
| 5,536,084 A | 7/1996 | Curtis et al. |
| 5,538,006 A | 7/1996 | Heim et al. |
| 5,542,420 A | 8/1996 | Goldman et al. |
| 5,544,649 A | 8/1996 | David et al. |
| 5,544,661 A | 8/1996 | Davis et al. |
| 5,547,470 A | 8/1996 | Johnson et al. |
| 5,561,412 A | 10/1996 | Novak et al. |
| 5,562,232 A | 10/1996 | Pearson |
| 5,564,803 A | 10/1996 | McDonald et al. |
| 5,573,506 A | 11/1996 | Vasko |
| 5,582,593 A | 12/1996 | Hultman |
| 5,583,758 A | 12/1996 | McIlroy et al. |
| 5,592,374 A | 1/1997 | Fellagara et al. |
| 5,594,786 A | 1/1997 | Chaco |
| 5,597,995 A | 1/1997 | Williams et al. |
| 5,601,445 A | 2/1997 | Schipper et al. |
| 5,622,429 A | 4/1997 | Heinz |
| 5,628,309 A | 5/1997 | Brown |
| 5,630,710 A | 5/1997 | Tune et al. |
| 5,633,910 A | 5/1997 | Cohen |
| 5,643,212 A | 7/1997 | Coutre et al. |
| 5,644,778 A | 7/1997 | Burks et al. |
| 5,645,531 A | 7/1997 | Thompson et al. |
| 5,651,775 A | 7/1997 | Walker et al. |
| 5,655,118 A | 8/1997 | Hendel et al. |
| 5,657,236 A | 8/1997 | Conkright |
| 5,658,250 A | 8/1997 | Blomquist et al. |
| 5,672,154 A | 9/1997 | Sillen et al. |
| 5,681,285 A | 10/1997 | Ford et al. |
| 5,683,367 A | 11/1997 | Jordan et al. |
| 5,685,844 A | 11/1997 | Marttila |
| 5,689,229 A | 11/1997 | Chaco et al. |
| 5,692,640 A | 12/1997 | Caulfield et al. |
| 5,699,038 A | 12/1997 | Ulrich et al. |
| 5,700,998 A | 12/1997 | Palti |
| 5,703,786 A | 12/1997 | Conkright |
| 5,704,352 A | 1/1998 | Tremblay et al. |
| 5,710,551 A | 1/1998 | Ridgeway |
| 5,712,913 A | 1/1998 | Chaum |
| 5,713,856 A | 2/1998 | Eggers |
| 5,721,913 A | 2/1998 | Ackroff et al. |
| 5,733,259 A | 3/1998 | Valcke et al. |
| 5,737,539 A | 4/1998 | Edelson |
| 5,738,102 A | 4/1998 | Lemelson |

(56) References Cited

U.S. PATENT DOCUMENTS

| | | |
|---|---|---|
| 5,752,235 A | 5/1998 | Kehr et al. |
| 5,758,095 A | 5/1998 | Albaum et al. |
| 5,758,096 A | 5/1998 | Barsky et al. |
| 5,760,704 A | 6/1998 | Barton et al. |
| 5,764,034 A | 6/1998 | Bowman et al. |
| 5,772,585 A | 6/1998 | Lavin et al. |
| 5,774,865 A | 6/1998 | Glynn |
| 5,781,442 A | 7/1998 | Engelson et al. |
| 5,790,409 A | 8/1998 | Fedor et al. |
| 5,795,327 A | 8/1998 | Wilson et al. |
| 5,803,906 A | 9/1998 | Pratt et al. |
| 5,807,321 A | 9/1998 | Stoker et al. |
| 5,807,336 A | 9/1998 | Russo et al. |
| 5,819,229 A | 10/1998 | Boppe |
| 5,822,418 A | 10/1998 | Yacenda et al. |
| 5,822,544 A | 10/1998 | Chaco et al. |
| 5,832,488 A | 11/1998 | Eberhardt |
| 5,833,599 A | 11/1998 | Schrier et al. |
| 5,842,173 A | 11/1998 | Strum et al. |
| 5,842,976 A | 12/1998 | Williamson |
| 5,845,253 A | 12/1998 | Rensimer et al. |
| 5,845,254 A | 12/1998 | Lockwood et al. |
| 5,845,255 A | 12/1998 | Mayaud |
| 5,845,264 A | 12/1998 | Nelhaus |
| 5,848,593 A | 12/1998 | McGrady et al. |
| 5,850,344 A | 12/1998 | Conkright |
| 5,852,408 A | 12/1998 | Christiansen et al. |
| 5,855,550 A | 1/1999 | Lai et al. |
| 5,867,821 A | 2/1999 | Ballantyne et al. |
| 5,871,465 A | 2/1999 | Vasko |
| 5,883,806 A | 3/1999 | Meador et al. |
| 5,885,245 A | 3/1999 | Lynch et al. |
| 5,894,273 A | 4/1999 | Meador et al. |
| 5,895,371 A | 4/1999 | Levitas et al. |
| 5,985,371 A | 4/1999 | Levitas et al. |
| 5,899,998 A | 5/1999 | McGauley et al. |
| 5,903,211 A | 5/1999 | Flego et al. |
| 5,905,653 A | 5/1999 | Higham et al. |
| 5,907,490 A | 5/1999 | Oliver |
| 5,911,132 A | 6/1999 | Sloane |
| 5,911,687 A | 6/1999 | Sato et al. |
| 5,912,818 A | 6/1999 | McGrady |
| 5,920,054 A | 6/1999 | Uber, III |
| 5,920,263 A | 7/1999 | Huttenhoff et al. |
| 5,928,329 A | 7/1999 | Clark et al. |
| 5,930,145 A | 7/1999 | Yuyama et al. |
| 5,935,099 A | 8/1999 | Peterson et al. |
| 5,941,710 A | 8/1999 | Lampotang et al. |
| 5,942,986 A | 8/1999 | Shabot et al. |
| 5,950,630 A | 9/1999 | Portwood et al. |
| 5,950,632 A | 9/1999 | Reber et al. |
| 5,953,099 A | 9/1999 | Walach |
| 5,954,641 A | 9/1999 | Kehr et al. |
| 5,957,885 A | 9/1999 | Bollish et al. |
| 5,961,036 A | 10/1999 | Michael et al. |
| 5,961,446 A | 10/1999 | Beller et al. |
| 5,971,593 A | 10/1999 | McGrady |
| 5,995,077 A | 11/1999 | Wilcox et al. |
| 6,000,828 A | 12/1999 | Leet |
| 6,003,006 A | 12/1999 | Colella |
| 6,009,333 A | 12/1999 | Chaco |
| 6,017,318 A | 1/2000 | Gauthier et al. |
| 6,021,392 A | 2/2000 | Lester et al. |
| 6,024,699 A | 2/2000 | Surwit et al. |
| 6,032,155 A | 2/2000 | de la Huerga |
| 6,039,251 A | 3/2000 | Holowko et al. |
| 6,047,203 A | 4/2000 | Sackner et al. |
| 6,048,087 A | 4/2000 | Laurent et al. |
| 6,053,887 A | 4/2000 | Levitas et al. |
| 6,063,026 A | 5/2000 | Schauss et al. |
| 6,082,776 A | 7/2000 | Feinberg |
| 6,112,182 A | 8/2000 | Akers et al. |
| RE36,871 E | 9/2000 | Epstein et al. |
| 6,112,502 A | 9/2000 | Frederick et al. |
| 6,134,582 A | 10/2000 | Kennedy |
| 6,135,949 A | 10/2000 | Russo et al. |
| 6,202,923 B1 * | 3/2001 | Boyer et al. .......... 235/375 |
| 6,228,057 B1 | 5/2001 | Vasko |
| 6,241,704 B1 | 6/2001 | Peterson et al. |
| 6,269,340 B1 | 7/2001 | Ford et al. |
| 6,282,441 B1 | 8/2001 | Raymond et al. |
| 6,290,681 B1 | 9/2001 | Brown |
| 6,292,698 B1 | 9/2001 | Duffin et al. |
| 6,302,844 B1 | 10/2001 | Walker et al. |
| 6,312,378 B1 | 11/2001 | Bardy |
| 6,314,556 B1 | 11/2001 | DeBusk et al. |
| 6,319,200 B1 | 11/2001 | Lai et al. |
| 6,322,502 B1 | 11/2001 | Schoenberg et al. |
| 6,338,007 B1 | 1/2002 | Broadfield et al. |
| 6,339,732 B1 | 1/2002 | Phoon et al. |
| 6,406,426 B1 | 6/2002 | Reuss et al. |
| 6,409,684 B1 | 6/2002 | Wilk |
| 6,421,650 B1 | 7/2002 | Goetz et al. |
| 6,493,747 B2 | 12/2002 | Simmon et al. |
| 6,519,569 B1 | 2/2003 | White et al. |
| 6,529,892 B1 | 3/2003 | Lambert |
| 6,540,672 B1 | 4/2003 | Simonsen et al. |
| 6,558,352 B1 | 5/2003 | Hogan |
| 6,571,128 B2 | 5/2003 | Lebel et al. |
| 6,581,606 B2 | 6/2003 | Kutzko et al. |
| 6,671,563 B1 | 12/2003 | Engelson et al. |
| 6,745,764 B2 | 6/2004 | Hickle |
| 6,757,898 B1 | 7/2004 | Ilsen et al. |
| 6,785,589 B2 | 8/2004 | Eggenberger et al. |
| 6,796,956 B2 | 9/2004 | Hartlaub et al. |
| 6,799,149 B2 | 9/2004 | Hartlaub |
| 6,847,861 B2 | 1/2005 | Lunak et al. |
| 6,856,247 B1 | 2/2005 | Wallace |
| 6,873,268 B2 | 3/2005 | Lebel et al. |
| 6,993,402 B2 | 1/2006 | Klass et al. |
| 7,034,691 B1 | 4/2006 | Rapaport et al. |
| 7,054,844 B2 | 5/2006 | Fletcher et al. |
| 7,060,059 B2 | 6/2006 | Keith et al. |
| 7,096,072 B2 | 8/2006 | Engleson et al. |
| 7,201,734 B2 | 4/2007 | Hickle |
| 7,204,823 B2 | 4/2007 | Estes et al. |
| 7,215,991 B2 | 5/2007 | Besson et al. |
| 7,229,430 B2 | 6/2007 | Hickle et al. |
| 7,230,529 B2 | 6/2007 | Ketcherside, Jr. et al. |
| 7,256,708 B2 | 8/2007 | Rosenfeld et al. |
| 7,263,492 B1 | 8/2007 | Suresh et al. |
| 7,379,885 B1 | 5/2008 | Zakim |
| 7,384,420 B2 | 6/2008 | Dycus et al. |
| 7,398,183 B2 | 7/2008 | Holland et al. |
| 7,421,709 B2 | 9/2008 | Watson et al. |
| 7,433,853 B2 | 10/2008 | Brockway et al. |
| 7,471,994 B2 | 12/2008 | Ford et al. |
| 7,526,769 B2 | 4/2009 | Watts et al. |
| 7,587,415 B2 | 9/2009 | Guarav et al. |
| 7,612,679 B1 | 11/2009 | Fackler et al. |
| 7,693,697 B2 | 4/2010 | Westenskow et al. |
| 7,769,601 B1 | 8/2010 | Bleser et al. |
| 7,771,385 B2 | 8/2010 | Eggers et al. |
| 7,771,386 B2 | 8/2010 | Eggers et al. |
| 7,776,031 B2 | 8/2010 | Hartlaub et al. |
| 7,787,946 B2 | 8/2010 | Stahmann et al. |
| 7,796,045 B2 | 9/2010 | Spear et al. |
| 7,835,927 B2 | 11/2010 | Schlotterbeck et al. |
| 7,847,970 B1 | 12/2010 | McGrady |
| 7,860,583 B2 | 12/2010 | Condurso et al. |
| 7,962,544 B2 | 6/2011 | Torok et al. |
| 7,970,550 B2 | 6/2011 | Arakelyan et al. |
| 7,983,995 B2 | 7/2011 | Murphy et al. |
| 8,005,688 B2 | 8/2011 | Coffman et al. |
| 8,024,200 B2 | 9/2011 | Jennings et al. |
| 7,935,927 B2 | 11/2011 | Schlotterbeck et al. |
| 8,160,895 B2 | 4/2012 | Schmitt et al. |
| 8,197,437 B2 | 6/2012 | Kalafut et al. |
| 8,284,059 B2 | 10/2012 | Ross |
| 8,291,337 B2 | 10/2012 | Gannin et al. |
| 8,340,792 B2 | 12/2012 | Condurso et al. |
| 8,630,722 B2 | 1/2014 | Condurso |
| 8,689,008 B2 | 4/2014 | Rangadass et al. |
| 8,761,906 B2 | 6/2014 | Condurso et al. |

(56) References Cited

U.S. PATENT DOCUMENTS

| | | |
|---|---|---|
| 2001/0037083 A1 | 11/2001 | Hartlaub et al. |
| 2001/0044731 A1 | 11/2001 | Coffman et al. |
| 2002/0010679 A1 | 1/2002 | Felsher |
| 2002/0016568 A1 | 2/2002 | Lebel et al. |
| 2002/0016923 A1 | 2/2002 | Knaus et al. |
| 2002/0022973 A1 | 2/2002 | Sun et al. |
| 2002/0026223 A1 | 2/2002 | Riff et al. |
| 2002/0033548 A1 | 3/2002 | Brodkin et al. |
| 2002/0035484 A1 | 3/2002 | McCormick |
| 2002/0038392 A1 | 3/2002 | De La Huerga |
| 2002/0042636 A1 | 4/2002 | Koshiol et al. |
| 2002/0046346 A1 | 4/2002 | Evans |
| 2002/0077849 A1 | 6/2002 | Baruch et al. |
| 2002/0087114 A1 | 7/2002 | Hartlaub |
| 2002/0116509 A1 | 8/2002 | De La Huerga |
| 2002/0120350 A1 | 8/2002 | Klass et al. |
| 2002/0169636 A1 | 11/2002 | Eggers et al. |
| 2002/0198624 A1 | 12/2002 | Greenwald et al. |
| 2003/0009244 A1 | 1/2003 | Engleson et al. |
| 2003/0036683 A1 | 2/2003 | Kehr et al. |
| 2003/0045858 A1 | 3/2003 | Struys et al. |
| 2003/0051737 A1 | 3/2003 | Hickle et al. |
| 2003/0063524 A1 | 4/2003 | Niemiec et al. |
| 2003/0069481 A1 | 4/2003 | Hervy et al. |
| 2003/0105389 A1 | 6/2003 | Noonan et al. |
| 2003/0105555 A1 | 6/2003 | Lunak et al. |
| 2003/0106553 A1 | 6/2003 | Vanderveen |
| 2003/0114836 A1 | 6/2003 | Estes et al. |
| 2003/0121517 A1 | 7/2003 | McFarland |
| 2003/0129578 A1 | 7/2003 | Mault |
| 2003/0135087 A1 | 7/2003 | Hickle et al. |
| 2003/0135388 A1 | 7/2003 | Martucci et al. |
| 2003/0139701 A1 | 7/2003 | White et al. |
| 2003/0140928 A1 | 7/2003 | Bui et al. |
| 2003/0140929 A1 | 7/2003 | Wilkes et al. |
| 2003/0149599 A1* | 8/2003 | Goodall ............... G06Q 50/22 705/2 |
| 2003/0156143 A1 | 8/2003 | Westenskow et al. |
| 2003/0158746 A1 | 8/2003 | Forrester |
| 2003/0163223 A1 | 8/2003 | Blomquist |
| 2003/0205897 A1 | 11/2003 | Kaufman |
| 2003/0236683 A1* | 12/2003 | Henderson ........... G06F 19/323 705/2 |
| 2004/0068229 A1 | 4/2004 | Jansen et al. |
| 2004/0073329 A1 | 4/2004 | Engleson et al. |
| 2004/0107118 A1 | 6/2004 | Harnsberger et al. |
| 2004/0122702 A1 | 6/2004 | Sabol et al. |
| 2004/0122705 A1 | 6/2004 | Sabol et al. |
| 2004/0122719 A1 | 6/2004 | Sabol et al. |
| 2004/0122790 A1 | 6/2004 | Walker et al. |
| 2004/0128162 A1 | 7/2004 | Schlotterbeck et al. |
| 2004/0152622 A1 | 8/2004 | Keith et al. |
| 2004/0167465 A1 | 8/2004 | Mihai et al. |
| 2004/0167804 A1 | 8/2004 | Simpson et al. |
| 2004/0172283 A1 | 9/2004 | Vanderveen et al. |
| 2004/0172300 A1 | 9/2004 | Mihai et al. |
| 2004/0172302 A1 | 9/2004 | Martucci et al. |
| 2004/0176297 A1 | 9/2004 | Cheung et al. |
| 2004/0188998 A1 | 9/2004 | Henthorn |
| 2004/0193325 A1 | 9/2004 | Bonderud et al. |
| 2004/0193446 A1 | 9/2004 | Mayer et al. |
| 2004/0260478 A1 | 12/2004 | Schwamm |
| 2005/0010166 A1 | 1/2005 | Hickle |
| 2005/0010269 A1 | 1/2005 | Lebel et al. |
| 2005/0020996 A1 | 1/2005 | Hartlaub et al. |
| 2005/0021297 A1 | 1/2005 | Hartlaub |
| 2005/0022274 A1 | 1/2005 | Campbell et al. |
| 2005/0033606 A1 | 2/2005 | Miller |
| 2005/0049179 A1 | 3/2005 | Davidson et al. |
| 2005/0055242 A1 | 3/2005 | Bello et al. |
| 2005/0088296 A1 | 4/2005 | Lee |
| 2005/0096941 A1* | 5/2005 | Tong ............................... 705/2 |
| 2005/0097566 A1 | 5/2005 | Watts et al. |
| 2005/0107914 A1 | 5/2005 | Engleson et al. |
| 2005/0108057 A1 | 5/2005 | Cohen et al. |
| 2005/0113945 A1 | 5/2005 | Engleson et al. |
| 2005/0119788 A1 | 6/2005 | Engleson et al. |
| 2005/0144043 A1 | 6/2005 | Holland et al. |
| 2005/0145010 A1 | 7/2005 | Vanderveen et al. |
| 2005/0148890 A1 | 7/2005 | Hastings |
| 2005/0171815 A1 | 8/2005 | Vanderveen |
| 2005/0224083 A1 | 10/2005 | Crass et al. |
| 2005/0278194 A1 | 12/2005 | Holland et al. |
| 2006/0026205 A1 | 2/2006 | Butterfield |
| 2006/0047538 A1 | 3/2006 | Condurso et al. |
| 2006/0053036 A1 | 3/2006 | Coffman et al. |
| 2006/0079831 A1 | 4/2006 | Gilbert |
| 2006/0101072 A1 | 5/2006 | Busche et al. |
| 2006/0122481 A1 | 6/2006 | Sievenpiper et al. |
| 2006/0190302 A1 | 8/2006 | Eggers et al. |
| 2006/0200369 A1 | 9/2006 | Batch et al. |
| 2006/0206356 A1 | 9/2006 | Vanderveen |
| 2006/0217628 A1 | 9/2006 | Huiku |
| 2006/0218015 A1 | 9/2006 | Walker et al. |
| 2006/0229551 A1 | 10/2006 | Martinez et al. |
| 2006/0249423 A1 | 11/2006 | Reijonen |
| 2006/0271401 A1 | 11/2006 | Lassetter et al. |
| 2006/0287890 A1 | 12/2006 | Stead et al. |
| 2007/0015972 A1 | 1/2007 | Wang et al. |
| 2007/0043767 A1 | 2/2007 | Osborne et al. |
| 2007/0061266 A1 | 3/2007 | Moore et al. |
| 2007/0061393 A1 | 3/2007 | Moore |
| 2007/0083389 A1 | 4/2007 | Dyer et al. |
| 2007/0106457 A1 | 5/2007 | Rosenberg |
| 2007/0106753 A1 | 5/2007 | Moore |
| 2007/0106754 A1 | 5/2007 | Moore |
| 2007/0156452 A1 | 7/2007 | Batch |
| 2007/0156860 A1 | 7/2007 | Nedelcu et al. |
| 2007/0168301 A1 | 7/2007 | Eisner et al. |
| 2007/0185615 A1 | 8/2007 | Bossi et al. |
| 2007/0208454 A1 | 9/2007 | Forrester et al. |
| 2007/0210157 A1 | 9/2007 | Miller |
| 2007/0286466 A1 | 12/2007 | Heffernan et al. |
| 2007/0293843 A1 | 12/2007 | Ireland et al. |
| 2008/0015549 A1 | 1/2008 | Maughan |
| 2008/0025230 A1 | 1/2008 | Patel et al. |
| 2008/0034323 A1 | 2/2008 | Blomquist |
| 2008/0040151 A1 | 2/2008 | Moore |
| 2008/0046292 A1 | 2/2008 | Myers et al. |
| 2008/0141272 A1 | 6/2008 | Borgendale et al. |
| 2008/0162254 A1 | 7/2008 | Herger et al. |
| 2008/0164998 A1 | 7/2008 | Scherpbier et al. |
| 2008/0169045 A1 | 7/2008 | Tribble et al. |
| 2008/0195246 A1 | 8/2008 | Tribble et al. |
| 2008/0272138 A1 | 11/2008 | Ross et al. |
| 2008/0317672 A1 | 12/2008 | Viertio-Oja |
| 2009/0012812 A1 | 1/2009 | Rausch et al. |
| 2009/0012813 A1 | 1/2009 | Berzansky et al. |
| 2009/0099867 A1 | 4/2009 | Newman |
| 2009/0112333 A1 | 4/2009 | Sahai |
| 2009/0125335 A1 | 5/2009 | Manetta et al. |
| 2009/0150484 A1 | 6/2009 | Roberts |
| 2009/0210252 A1 | 8/2009 | Silver |
| 2009/0240651 A1 | 9/2009 | Fletcher et al. |
| 2009/0306585 A1 | 12/2009 | Pang et al. |
| 2009/0306944 A1 | 12/2009 | Willmann et al. |
| 2009/0319623 A1 | 12/2009 | Srinivasan et al. |
| 2010/0037067 A1 | 2/2010 | Rangadass et al. |
| 2010/0094653 A1 | 4/2010 | Tribble et al. |
| 2010/0121654 A1 | 5/2010 | Portnoy et al. |
| 2010/0161113 A1 | 6/2010 | Tribble et al. |
| 2010/0169120 A1 | 7/2010 | Herbst et al. |
| 2010/0169771 A1 | 7/2010 | Pelegrin et al. |
| 2010/0174552 A1 | 7/2010 | Hawkes et al. |
| 2010/0174553 A1 | 7/2010 | Kaufman et al. |
| 2010/0179825 A1 | 7/2010 | Hanov et al. |
| 2010/0241453 A1 | 9/2010 | Malec |
| 2010/0241456 A1 | 9/2010 | Miller et al. |
| 2010/0271218 A1 | 10/2010 | Hoag et al. |
| 2010/0280840 A1 | 11/2010 | Fukushi et al. |
| 2010/0323397 A1 | 12/2010 | Reavy et al. |
| 2011/0015941 A1 | 1/2011 | Backhaus |
| 2011/0046975 A1 | 2/2011 | Hoffman |
| 2011/0060758 A1 | 3/2011 | Schlotterbeck et al. |

(56) References Cited

U.S. PATENT DOCUMENTS

| | | |
|---|---|---|
| 2011/0078608 A1 | 3/2011 | Gannon et al. |
| 2011/0119612 A1 | 5/2011 | Gannon et al. |
| 2011/0179405 A1 | 7/2011 | Dicks et al. |
| 2011/0202495 A1 | 8/2011 | Gawlick |
| 2011/0282691 A1 | 11/2011 | Coffman et al. |
| 2011/0288882 A1 | 11/2011 | Halow |
| 2011/0313787 A1 | 12/2011 | Rangadass et al. |
| 2012/0011253 A1 | 1/2012 | Friedman et al. |
| 2012/0016215 A1 | 1/2012 | Condurso et al. |
| 2012/0041775 A1 | 2/2012 | Cosentino et al. |
| 2012/0053533 A1 | 3/2012 | Butterfield et al. |
| 2012/0075061 A1 | 3/2012 | Barnes |
| 2012/0136673 A1 | 5/2012 | Presley et al. |
| 2012/0173264 A1 | 7/2012 | Brush et al. |
| 2012/0182939 A1 | 7/2012 | Rajan et al. |
| 2012/0185267 A1 | 7/2012 | Kamen et al. |
| 2012/0191052 A1 | 7/2012 | Rao |
| 2012/0239824 A1 | 9/2012 | Nguyen et al. |
| 2012/0241043 A1* | 9/2012 | Perazzo ............... A61J 7/0053 141/2 |
| 2012/0247480 A1 | 10/2012 | Varga |
| 2012/0253835 A1 | 10/2012 | Tracy et al. |
| 2012/0265549 A1 | 10/2012 | Virolainen |
| 2013/0018356 A1 | 1/2013 | Prince et al. |
| 2013/0085771 A1 | 4/2013 | Ghanbari et al. |
| 2013/0096444 A1 | 4/2013 | Condurso et al. |
| 2013/0197927 A1 | 8/2013 | Vanderveen et al. |
| 2013/0197928 A1 | 8/2013 | Vanderveen et al. |
| 2013/0197929 A1 | 8/2013 | Vanderveen et al. |
| 2013/0197930 A1 | 8/2013 | Garibaldi et al. |
| 2013/0197931 A1 | 8/2013 | Gupta et al. |
| 2013/0204433 A1 | 8/2013 | Gupta et al. |
| 2013/0204637 A1 | 8/2013 | Vanderveen et al. |
| 2013/0262138 A1 | 10/2013 | Jaskela et al. |
| 2014/0028464 A1 | 1/2014 | Garibaldi |
| 2014/0031976 A1 | 1/2014 | Reinhardt et al. |
| 2014/0100868 A1 | 4/2014 | Condurso et al. |
| 2014/0278466 A1* | 9/2014 | Simmons ............. G06F 19/3456 705/2 |
| 2014/0297313 A1 | 10/2014 | Condurso |
| 2014/0350950 A1 | 11/2014 | Jaskela et al. |
| 2015/0250948 A1 | 9/2015 | Gupta et al. |
| 2016/0000997 A1 | 1/2016 | Batch et al. |

FOREIGN PATENT DOCUMENTS

| | | |
|---|---|---|
| CN | 1759398 A | 4/2006 |
| CN | 1803103 A | 7/2006 |
| CN | 101116077 A | 1/2008 |
| CN | 101146055 A | 3/2008 |
| CN | 201110955 Y | 9/2008 |
| CN | 101331491 A | 12/2008 |
| CN | 101689320 A | 3/2010 |
| CN | 101890193 A | 11/2010 |
| CN | 102068725 A | 5/2011 |
| CN | 10 2521394 A | 6/2012 |
| CN | 102508877 A | 6/2012 |
| CN | 102688532 A | 9/2012 |
| CN | 102799783 A | 11/2012 |
| DE | 4023785 | 1/1992 |
| EP | 0192786 | 9/1986 |
| EP | 0384155 | 8/1990 |
| EP | 0595474 | 5/1994 |
| EP | 0649316 | 4/1995 |
| EP | 0652528 | 5/1995 |
| EP | 0784283 | 7/1997 |
| EP | 0921488 | 6/1999 |
| EP | 1003121 | 5/2000 |
| EP | 1018347 | 7/2000 |
| EP | 1237113 | 9/2002 |
| GB | 2141006 | 12/1984 |
| JP | 62114562 | 5/1987 |
| JP | 5168708 | 7/1993 |
| JP | 11-505352 | 5/1999 |
| JP | 2002-520718 | 7/2002 |
| JP | 2003085283 A | 3/2003 |
| JP | 2004287616 A | 10/2004 |
| JP | 2006155070 A | 6/2006 |
| JP | 2008508616 A | 3/2008 |
| KR | 1020070045611 | 5/2007 |
| KR | 1020080013129 | 2/2008 |
| KR | 100847397 B1 | 7/2008 |
| KR | 1020100125972 | 12/2010 |
| KR | 1020110070824 | 6/2011 |
| KR | 1020120076615 | 7/2012 |
| KR | 1020120076635 | 7/2012 |
| NZ | 522631 A | 7/2004 |
| WO | WO 1993/022735 | 11/1993 |
| WO | WO 1994/005344 | 3/1994 |
| WO | WO 1994/008647 | 4/1994 |
| WO | WO 1994/013250 | 6/1994 |
| WO | WO 1995/023378 | 8/1995 |
| WO | WO 1996/020745 | 7/1996 |
| WO | WO-199620745 A1 | 7/1996 |
| WO | WO 1996/025214 | 8/1996 |
| WO | WO-199625214 A1 | 8/1996 |
| WO | WO 1996/036923 | 11/1996 |
| WO | WO 1997/004712 | 2/1997 |
| WO | WO 1998/013783 | 4/1998 |
| WO | WO 1998/028676 | 7/1998 |
| WO | WO 1999/009505 | 2/1999 |
| WO | WO 1999/010829 | 3/1999 |
| WO | WO 1999/010830 | 3/1999 |
| WO | WO 1999/035588 | 7/1999 |
| WO | WO 1999/044167 | 9/1999 |
| WO | WO 1999/045490 | 9/1999 |
| WO | WO 1999/046718 | 9/1999 |
| WO | WO 1999/067732 | 12/1999 |
| WO | WO 2000/003344 | 1/2000 |
| WO | WO 2000/004521 | 1/2000 |
| WO | WO 2000/018449 | 4/2000 |
| WO | WO 2000/032088 | 6/2000 |
| WO | WO 2000/032098 | 6/2000 |
| WO | WO 2001/086506 | 11/2001 |
| WO | WO 2001/088828 | 11/2001 |
| WO | WO 2002/036044 | 5/2002 |
| WO | WO 2002/069099 | 9/2002 |
| WO | WO 2003/038566 | 5/2003 |
| WO | WO 2003/053503 | 7/2003 |
| WO | WO 2003/092769 | 11/2003 |
| WO | WO 2003/094091 | 11/2003 |
| WO | WO 2004/060443 | 7/2004 |
| WO | WO 2004/061745 | 7/2004 |
| WO | WO-2010124016 A1 | 10/2010 |
| WO | WO-2010124328 A1 | 11/2010 |
| WO | WO-2012095829 A2 | 7/2012 |
| WO | WO-2014159280 A1 | 10/2014 |

OTHER PUBLICATIONS

Non-Final Office Action dated Oct. 14, 2014, issued in U.S. Appl. No. 11/326,145.
U.S. Appl. No. 90/009,912, filed Aug. 12, 2013, Schlotterbeck et al.
U.S. Appl. No. 90/011,697, filed Aug. 12, 2013, Schlotterbeck et al.
Queensland Health. Use of returned or unused dispensed medicines, Jan. 5, 2005, Queensland Government. pp. 1-2.
"General-Purpose Infusion Pumps," Evaluation—Health Devices, Oct. 2002, pp. 353-387, vol. 31 (10), ECRI Institute.
"Infusion Pump Technology," Health Devices, Apr.-May 1998, pp. 150-170, vol. 27(4-5), ECRI Institute.
"Infusion Pumps, General Purpose," Healthcare Product Comparison System, 2007, pp. 1-54, ECRI Institute.
"Infusion Pumps, Large-Volume," Healthcare Product Comparison System, 2010, pp. 1-51, ECRI Institute.
"Smart Infusion Pumps Join CPOE and Bar Coding as Important Ways to Prevent Medication Errors," ISMP—Medication Safety Alert, Feb. 7, 2002, 2 pgs., Institute for Safe Medication Practices.
Anonymous, Guardrails ® Safety Software—Medley TM Medication Safety System, Alaris Medical Systems XP-00234431; 2002 Alaris Medical Systems Inc. Nov. 2002, SSM @2159C.

(56) References Cited

OTHER PUBLICATIONS

Baldauf-Sobez et al., "How Siemens' Computerized Physician Order Entry Helps Prevent the Human Errors," Electromedica, vol. 71, No. 1, 2003, pp. 2-10.
Calabrese, et al., "Medication administration errors in adult patients in the ICU," Intensive Care Med, 2001, pp. 1592-1598, vol. 27, Springer-Verlag.
Eskew, James et al., Using Innovative Technologies to Set New Safety Standards for the Infusion of Intravenous Medications, Hospital Pharmacy, vol. 37, No. 11, pp. 1179-1189, 2002, Facts and Comparisons.
Kohn, et al., "To Err is Human—Building a Safer Health System," National Academy Press, 2002, pp. i-287, National Academy of Sciences.
Lesar, "Recommendations for Reducing Medication Errors," Medscape Pharmacists, posted Jul. 24, 2000, 10 pgs, vol. 1(2), Medscape Pharmacists, <http://www.medscape.com>.
Meier, "Hospital Products Get Seal of Approval at a Price," The New York Times, Apr. 23, 2002, 5 pgs.
Shabot et al., "Wireless clinical alerts for critical medication, laboratory and physiologic data," System Sciences 2000. Proceedings of the 33rd Annual Conference on Jan. 4-7, 2000, Piscataway, NJ, IEEE, Jan. 4, 2000.
Williams, et al., "Reducing the Risk of User Error with Infusion Pumps," Professional Nurse—Safe Practice—Infusion Devices, Mar. 2000, pp. 382-384, vol. 15(6).
Yokoi, "Prevention of Errors in Injection/Drip Infusion—No excuse for ignorance!—Essential Points of Accident Prevention, IV Infusion Pump, Syringe-pump Accident Prevention," JIN Special, Igaku Shoin K.K., Dec. 1, 2001, pp. 109-120, No. 70.
International Search Report for Application No. PCT/US2014/038497, dated Oct. 23, 2014, 3 pages.
Extended European Search Report for Application No. 14779655.1, dated Jul. 14, 2016, 8 pages.
Extended European Search Report for Application No. 14780320.9, dated Jul. 1, 2016, 7 pages.
Extended European Search Report for Application No. 14775918.7, dated Sep. 13, 2016, 10 pages.
Canadian Office Action for Application No. 2512991, dated Mar. 2, 2017, 4 pages.
Extended European Search Report for Application No. 14801726.2, dated Jan. 5, 2017, 8 pages.
Extended European Search Report for Application No. 14801713.0, dated Jan. 16, 2017, 8 pages.
Evans, R. S. et al., "Enhanced notification of infusion pump programming errors", Studies in health technology and informatics, Jan. 1, 2010, pp. 734-738, XP055305644, Netherlands DOI: 10.3233/978-1-60750-588-4-734 Retrieved from the Internet: URL:http://booksonline.iospress.nl/Extern/EnterMedLine.aspx?ISSN=0926-9630&Volume=160&SPage=734 [retrieved on Sep. 26, 2016].
Extended European Search Report and Written Opinion for Application No. 14772937.0, dated Oct. 10, 2016, 9 pages.
Extended European Search Report and Written Opinion for Application No. 14779139.6, dated Nov. 7, 2016, 7 pages.
Chinese Office Action for Application No. 201480015147.6, dated Mar. 10, 2017, 10 pages excluding translation.
Canadian Office Action for Application No. 2551903, dated Mar. 28, 2017, 7 pages.
European Office Action for Application No. 12756903.6, dated Apr. 19, 2017, 5 pages.
Office Action for United Arab Emirates Application No. UAE/P/0962/2013, dated Apr. 17, 2017, 18 pages.
European Office Action for Application No. 14779655.1, dated Jul. 28, 2017, 6 pages.
Memo concerning Mexican Office Action for Application No. MX/a/2015/015959, dated Sep. 21, 2017, 4 pages.
Australian Examination Report No. 1 for Application No. 2016216550, dated Sep. 20, 2017, 3 pages.
Chinese Office Action for Application No. 201480015147.6, dated Nov. 16, 2017, 8 pages.
European Communication of the Board of Appeal for Application No. 05791269.3, dated Nov. 10, 2017, 7 pages.
European Office Action for Application No. 14775918.7, dated Dec. 20, 2017, 8 pages.
Chinese Office Action for Application No. 201480015025.7, dated Jan. 23, 2018, 11 pages excluding English summary.
Chinese Office Action for Application No. 201480015036.5, dated Jan. 23, 2018, 13 pages excluding English translation.
European Office Action for Application No. 14779655.1, dated Mar. 8, 2018, 7 pages.
Japanese Office Action in Application No. 2016-501081, dated Feb. 9, 2018, 4 pages.
Memo concerning Mexican Office Action for Application No. MX/a/2015/015959, memo dated Mar. 2, 2018, 1 page.
Canadian Office Action for Application No. 2512991, dated Jan. 10, 2018, 4 pages.
Canadian Office Action for Application No. 2828898, dated Jan. 11, 2018, 8 pages.
Canadian Office Action for Application No. 2551903, dated Mar. 5, 2018, 8 pages.
Chinese Office Action for Application No. 201480015147.6, dated May 3, 2018, 6 pages.
European Office Action for Application No. 14772937.0, dated Apr. 19, 2018, 9 pages.
Chinese Office Action for Application No. 201480015093.3, dated Jul. 16, 2018, 16 pages.
Chinese Office Action for Application No. 201480015025.7, dated Oct. 9, 2018, 27 pages.
Chinese Office Action for Application No. 201480015036.5, dated Sep. 29, 2018, 20 pages.
Chinese Office Action for Application No. 201480041362.3, dated Oct. 18, 2018, 13 pages.
Japanese Office Action for Application No. 2016-501081, dated Nov. 2, 2018, 6 pages.
Canadian Office Action for Application No. 2828898, dated Dec. 7, 2018, 5 pages.
Australian Office Action for Application No. 2014241022, dated Feb. 7, 2019, 4 pages.
Australian Office Action for Application No. 2014241019, dated Feb. 6, 2019, 3 pages.
U.S. Appl. No. 09/860,865, filed May 18, 2001, Damon J. Coffman, et al.
U.S. Appl. No. 10/750,032, filed Dec. 31, 2003, Timothy W. Vanderveen.
U.S. Appl. No. 10/361,704, filed Feb. 9, 2003, Timothy W. Vanderveen, et al.
U.S. Appl. No. 13/185,427, filed Jul. 18, 2011, Damon J. Coffman, et al.
U.S. Appl. No. 13/246,782, filed Sep. 27, 2011, Joseph Condurso, et al.
U.S. Appl. No. 13/559,537, filed Jul. 26, 2012, Federico Garibaldi.
U.S. Appl. No. 13/802,663, filed Mar. 13, 2013, Federico Garibaldi.
U.S. Appl. No. 13/802,443, filed Mar. 13, 2013, Timothy W. Vanderveen, et al.
U.S. Appl. No. 13/802,679, filed Mar. 13, 2013, Vikas Gupta, et al.
U.S. Appl. No. 13/802,693, filed Mar. 13, 2013, Vikas Gupta, et al.
U.S. Appl. No. 13/802,446, filed Mar. 13, 2013, Timothy W. Vanderveen, et al.
U.S. Appl. No. 13/802,433, filed Mar. 13, 2013, Timothy W. Vanderveen, et al.
U.S. Appl. No. 13/802,454, filed Mar. 13, 2013, Timothy W. Vanderveen, et al.
U.S. Appl. No. 13/901,504, filed May 23, 2013, Maria Consolacion Jaskela, et al.
U.S. Appl. No. 14/306,125, filed Jun. 16, 2014, Joseph Condurso, et al.
U.S. Appl. No. 11/326,145, filed Dec. 30, 2005, Richard M. Batch, et al.
U.S. Appl. No. 13/421,776, filed Mar. 15, 2012, Ryan Nguyen, et al.
U.S. Appl. No. 11/326,145, filed Dec. 30, 2005, Batch, et al.
U.S. Appl. No. 14/721,995, filed May 26, 2015, Gupta, et al.
U.S. Appl. No. 14/848,063, filed Sep. 8, 2015, Batch, et al.

(56) References Cited

OTHER PUBLICATIONS

Chinese Office Action for Application No. 201480015093.3, dated Apr. 25, 2019, 18 pages.
Chinese Office Action for Application No. 201480041985.0, dated Apr. 3, 2019, 12 pages.
Japanese Office Action for Application No. 2016-501081, dated May 7, 2019, 4 pages.
Australian Office Action for Application No. 2014268828, dated Jul. 26, 2019, 4 pages.
Chinese Office Action for Application No. 201480015025.7, dated Jun. 24, 2019, 25 pages.
Chinese Office Action for Application No. 201480015036.5, dated Jun. 24, 2019, 20 pages.
European Summons to attend oral proceedings pursuant to Rule 115(1) EPC for Application No. 14772937.0, dated Jul. 17, 2019, 12 pages.

* cited by examiner

FIG. 4B

Transaction Queue — 430

Local Queue | Global View | Printer Alert | Close Transaction Queue

Active Item

Mode
- ● Pick  ○ Restock
- ☐ INSTANT RETURNS
- ☐ INSTANT RESTOCK

Item ID: 3347V250C
Location: HDS-02-01-02-01
Quantity: 50   (ESC) to Reset

Description: dextrose (D5W) 5% in water LATEX FREE BAG 250 mL
Patient:
Destination: IV Room Reprint Label | Quantity On Hand 160 | Save Quantity On Hand | Hold Active Item | Waste

— 431

Current Sort
● Auto  ○ Priority  ○ Column  ○ By Priority

Waiting For Item Scan...
SCAN OVERRIDE REQUIRED (F10)

Pyxis Replenishment 32
Manual STAT Order 3
STAT Redispense 6

Find | Filter | Pick Now | Hold Selected | Release Selected | Delete Selected | Refresh Queue | Add Manual Pick

— 432

| Select | Priority | Quantity | Item | Location | Destination | Patient |
|---|---|---|---|---|---|---|
| ☐ | IV Batch Pick | 30 | dextrose 5% in water (D5W) 250 mL intravenous | HDS-01-02-02-01 | IV Room | |
| ☐ | IV Batch Pick | 10 | gentamicin sulfate 40mg/mL 2 mL vial | VC1-01-06-20-03 | IV Room | |
| ☐ | IV Batch Pick | 15 | vancomycin 1 gram vial | VC1-01-23-11-01 | IV Room | |
| ☐ | IV Batch Pick | 10 | ampicillin sodium 1gram vial | VC1-01-14-09-01 | IV Room | |
| ☐ | IV Batch Pick | 10 | norEPINEPHrine bitartrate (NOREPINEPHRINE lMG/ML 10X4ML) 1mg/mL 4 mL vial | VC1-01-28-01-01 | IV Room | |
| ☐ | IV Batch Pick | 20 | normal saline (SODIUM CHLORIDE) 0.9% MB+ 100 mL | HDS-02-02-04-01 | IV Room | |
| ☐ | IV Batch Pick | 22 | ampicillin sodium 1gram vial | VC1-01-14-09-01 | IV Room | |
| ☐ | IV Batch Pick | 14 | dextrose 5% in water (D5W) 150 mL intravenous | HDS-01-01-04-01 | IV Room | |
| ☐ | IV Batch Pick | 20 | dextrose 5% in water (D5W) 50 mL intravenous | HDS-01-01-02-01 | IV Room | |
| ☐ | | | | | | |
| ☐ | | | | | | |
| ☐ | | | | | | |

** SCANNER IS OFFLINE

MEDICATION PREPARATION QUEUE

BACKGROUND

Field

The present disclosure generally relates to medication distribution, and, in particular, relates to systems and methods for managing preparation and delivery of a medication in a healthcare facility.

Description of the Related Art

Certain pharmaceutical drugs are compounded to fit the needs of a patient. Compounding pharmacists combine or process appropriate ingredients using various tools to create a compounded pharmaceutical drug. For instance, compounding of sterile intravenous (IV) compounds can be done in anticipation of medication orders based on standard doses, or compounding can be done specific to a patient's need based on a physician order. Compounding may be done for medically necessary reasons, such as to change the form of the medication from a solid pill to a liquid, to avoid a non-essential ingredient that the patient is allergic to, or to obtain the exact dose(s) needed of particular active pharmaceutical ingredient(s). It may also be done for more optional reasons, such as adding flavors to a medication or otherwise altering taste or texture. Compounding is most routine in the case of intravenous (IV)/parenteral medication.

In cases of patients admitted to a healthcare facility, one or more medications for a patient or infusions to be administered to the patient are prescribed by the patient's physician. A pharmacy, generally located within the patient's hospital or healthcare facility, prepares the medication according to the physician's prescription, for example, in a cleanroom (e.g., an environment having a controlled level of contamination that is specified by a number of particles per cubic meter at a specified particle size). In cases where the medication is an infusion solution, an appropriately trained and credentialed pharmacist places the infusion solution in a bag, bottle, syringe, or other container and labels the container. The infusion solution is then commonly staged in a pickup location, such as a bin-sorting area. A sorting person is then responsible for placing each prepared medication into bins or delivery carts that correspond to the locations where the medications will be delivered, such as an Intensive Care Unit (ICU). A delivery person retrieves the medications from the bins that correspond to areas of the healthcare facility to which that delivery person delivers. The delivery person then delivers the medications to the appropriate locations of the healthcare facility.

The medication is then delivered to the patient's location, and if the medication is an infusion solution, a clinician such as a nurse or other clinician hangs the infusion solution from a rack. The nurse connects a tube between the infusion solution and an infusion pumping system and inserts a cannula at the end of the tube into the vessel of the patient for delivery of the infusion solution to the patient.

SUMMARY

According to certain embodiments of the present disclosure, a system for managing preparation of a medication for a patient, the system includes a memory that includes instructions, and one or more processors. The one or more processors is configured to execute the instructions to receive information indicative of an order for medication for a patient from an electronic data feed, and determine whether the order for medication for the patient can be filled with a returned ("retrieved" or "retrievable") medication. The one or more processors is also configured to provide a notification to fill the order with the returned medication when the determination indicates the order can be filled with a returned medication, and provide a notification to fill the order by preparing the medication when the determination indicates a returned medication is not available to fill the order.

According to certain embodiments of the present disclosure, a method for managing preparation of a medication for a patient is provided. The method includes receiving information indicative of an order for medication for a patient from an electronic data feed, and determining whether the order for medication for the patient can be filled with a returned medication. The method also includes providing a notification to fill the order with the returned medication when the determination indicates the order can be filled with a returned medication, and providing a notification to fill the order by preparing the medication when the determination indicates a returned medication is not available to fill the order.

According to certain embodiments of the present disclosure, a machine-readable storage medium that includes machine-readable instructions for causing a processor to execute a method for managing preparation of a medication for a patient is provided. The method includes receiving information indicative of an order for medication for a patient from an electronic data feed, and determining whether the order for medication for the patient can be filled with a returned medication. The method also includes providing a notification to fill the order with the returned medication when the determination indicates the order can be filled with a returned medication, and providing a notification to fill the order by preparing the medication when the determination indicates a returned medication is not available to fill the order.

According to certain embodiments of the present disclosure, a system for managing preparation of a medication for a patient is provided. The system includes a memory that includes instructions, and one or more processors. The one or more processors is configured to execute the instructions to receive information indicative of an order for medication for a patient from an electronic data feed, and determine a position in a virtual queue configured to display multiple medication orders to be filled based on at least one of an estimated amount of time to prepare the medication, an estimated amount of time to deliver the medication to a delivery location, an estimated time at which the medication will be needed for administration to a patient at the delivery location, a delivery deadline for the medication, a degree of urgency for delivery of the medication, a type of the medication, or a component of the medication. The one or more processors is also configured to execute the instructions to provide an indicator of the order for medication for display at the position in the virtual queue.

According to certain embodiments of the present disclosure, a method for managing preparation of a medication for a patient is provided. The method includes receiving information indicative of an order for medication for a patient from an electronic data feed, and determining a position in a virtual queue configured to display multiple medication orders to be filled based on at least one of an estimated amount of time to prepare the medication, an estimated amount of time to deliver the medication to a delivery location, an estimated time at which the medication will be needed for administration to a patient at the delivery location, a delivery deadline for the medication, a degree of urgency for delivery of the medication, a type of the medication, or a component of the medication. The method also includes providing an indicator of the order for medication for display at the position in the virtual queue.

According to certain embodiments of the present disclosure, a machine-readable storage medium that includes machine-readable instructions for causing a processor to execute a method for managing preparation of a medication for a patient is provided. The method includes receiving information indicative of an order for medication for a patient from an electronic data feed, and determining a position in a virtual queue configured to display multiple medication orders to be filled based on at least one of an estimated amount of time to prepare the medication, an estimated amount of time to deliver the medication to a delivery location, an estimated time at which the medication will be needed for administration to a patient at the delivery location, a delivery deadline for the medication, a degree of urgency for delivery of the medication, a type of the medication, or a component of the medication. The method also includes providing an indicator of the order for medication for display at the position in the virtual queue.

According to certain embodiments of the present disclosure, a system for managing preparation of a medication for a patient is provided. The system includes a memory that includes instructions, and one or more processors. The one or more processors is configured to execute the instructions to receive information indicative of an order for medication for a patient from an electronic data feed, and determine whether the order can be filled with an available prepared medication or a returned medication. When the determination whether the order can be filled with an available prepared medication or a returned medication indicates a prepared medication or returned medication is available to fill the order, the one or more processors is configured to provide a notification to fill the order with the available prepared medication or returned medication, the notification including a pickup location at which the returned medication can be retrieved. When the determination indicates an available prepared medication or returned medication is not available to fill the order, the one or more processors is configured to provide a notification to fill the order by preparing the medication. The one or more processors is also configured to determine a position in a virtual queue configured to display multiple medication orders to be filled based on at least one of an estimated amount of time to prepare the medication, an estimated amount of time to deliver the medication to a delivery location, an estimated time at which the medication will be needed for administration to a patient at the delivery location, a delivery deadline for the medication, a degree of urgency for delivery of the medication, a type of the medication, or a component of the medication, and provide an indicator of the order for the medication for display at the position in the virtual queue, wherein the indicator of the order for the medication is provided for display at a position in the virtual queue associated with another medication having a same type or a same component as the medication. The one or more processors is yet configured to receive an image or barcode identifying a component used to formulate the medication, provide the image or barcode to a person responsible for verifying the medication is filled using the component, and receive an input indicating the person has verified the medication has been filled using the component. The one or more processors is also configured to provide an indication that the order for the medication is ready for delivery to the patient.

According to certain embodiments of the present disclosure, a method for managing preparation of a medication for a patient is provided. The method includes receiving information indicative of an order for medication for a patient from an electronic data feed, and determining whether the order can be filled with an available prepared medication or a returned medication. The method also includes providing a notification to fill the order with the available prepared medication or returned medication, the notification including a pickup location at which the returned medication can be retrieved when the determination whether the order can be filled with an available prepared medication or a returned medication indicates a prepared medication or returned medication is available to fill the order, and providing a notification to fill the order by preparing the medication when the determination indicates an available prepared medication or returned medication is not available to fill the order. The method further includes determining a position in a virtual queue configured to display multiple medication orders to be filled based on at least one of an estimated amount of time to prepare the medication, an estimated amount of time to deliver the medication to a delivery location, an estimated time at which the medication will be needed for administration to a patient at the delivery location, a delivery deadline for the medication, a degree of urgency for delivery of the medication, a type of the medication, or a component of the medication. The method yet further includes providing an indicator of the order for the medication for display at the position in the virtual queue, wherein the indicator of the order for the medication is provided for display at a position in the virtual queue associated with another medication having a same type or a same component as the medication, and receiving an image or barcode identifying a component used to formulate the medication. The method also includes providing the image or barcode to a person responsible for verifying the medication is filled using the component, receiving an input indicating the person has verified the medication has been filled using the component, and providing an indication that the order for the medication is ready for delivery to the patient.

According to certain embodiments of the present disclosure, a machine-readable storage medium that includes machine-readable instructions for causing a processor to execute a method for managing preparation of a medication for a patient is provided. The method includes receiving information indicative of an order for medication for a patient from an electronic data feed, and determining whether the order can be filled with an available prepared medication or a returned medication. The method also includes providing a notification to fill the order with the available prepared medication or returned medication, the notification including a pickup location at which the returned medication can be retrieved when the determination whether the order can be filled with an available prepared medication or a returned medication indicates a prepared medication or returned medication is available to fill the order, and providing a notification to fill the order by preparing the medication when the determination indicates an available prepared medication or returned medication is not available to fill the order. The method further includes determining a position in a virtual queue configured to display multiple medication orders to be filled based on at least one of an estimated amount of time to prepare the medication, an estimated amount of time to deliver the medication to a delivery location, an estimated time at which the medication will be needed for administration to a patient at the delivery location, a delivery deadline for the medication, a degree of urgency for delivery of the medication, a type of the medication, or a component of the medication. The method yet further includes providing an indicator of the order for the medication for display at the position in the virtual queue, wherein the indicator of the order for the medication is provided for display at a position in the virtual queue associated with another medication having a same type or a same component as the medication, and receiving an image or barcode identifying a component used to formulate the medication. The method also includes providing the image or barcode to a person responsible for verifying the medication is filled using the component, receiving an input indicating the person has verified the medication has been filled using the component, and providing an indication that the order for the medication is ready for delivery to the patient.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIGS. 4A-4D are example illustrations associated with the example process of FIG. 3.

DETAILED DESCRIPTION

Figure 1:
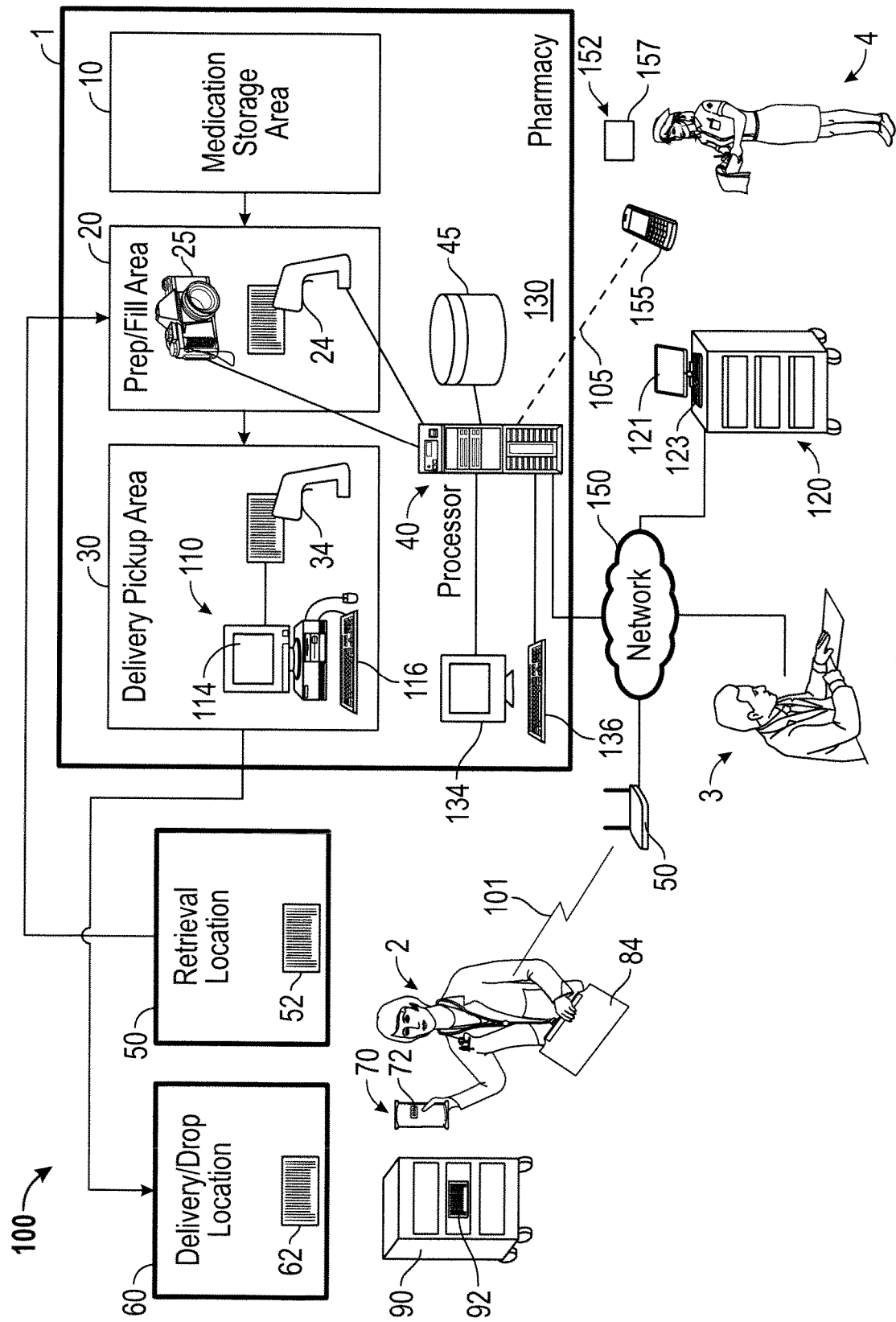
FIG. 1 illustrates an example architecture for managing preparation of a medication.

In the following detailed description, numerous specific details are set forth to provide a full understanding of the present disclosure. It will be apparent, however, to one ordinarily skilled in the art that the embodiments of the present disclosure may be practiced without some of these specific details. In other instances, well-known structures and techniques have not been shown in detail so as not to obscure the disclosure.

The disclosed system provides a virtual (e.g., electronic) queue in which orders for medications to be prepared (e.g., by a pharmacist) are listed and updated, in real-time, according to various factors, such as when an order is changed or discontinued. The orders are taken from an electronic data feed such as a Health Level 7 (HL7) feed. Data from the feed is processed in order to identify various aspects of each order to add to the virtual queue. The system then determines whether the order for the medication can be filled with an already prepared medication item or a returned or retrievable unused medication item, or whether the order should be filled by preparing a medication item. Appropriate instructions for filling the order are provided for display in the queue based on how the order can be filled. In certain instances, a notification or preferred retrieval route may be provided to a delivery person to retrieve a medication item if the retrievable medication item can be used to fill the order.

The electronic data feed is monitored to update, in real-time, an order for a medication in the queue if, for example, a patient is discharged and the order for the patient is no longer needed. The queue will continually update based on changes from the electronic data feed. Thus, if an order is changed or discontinued, the entry for the order will be immediately updated in the queue. This will result in preventing a compound medication from being made that is no longer needed at that point in time, thereby preventing waste. This will also result in preventing a dispensing of a product out for delivery or finalized and ready for delivery that may no longer be needed by a patient. This will further result in decreasing inefficient use of labor, and keeping a prepared medication on hand to potentially be used for a new order coming in.

Each order for a medication is placed at a position in the virtual queue based on various factors including, for example, an estimated amount of time to prepare the medication, an estimated amount of time to deliver the medication to a delivery location, an estimated time at which the medication will be needed for administration to a patient at the delivery location, a delivery deadline for the medication, a degree of urgency for delivery of the medication, a type of the medication, or a component of the medication. Two or more medication orders that require the same or similar medication components may be grouped together in the queue, for example, to avoid unnecessary wasting of the component. The disclosed system is also configured to capture images or barcode readings of each component used to prepare the medication for the order, and the images or barcode readings may be provided to a local or remote pharmacist or other authorized inspector for verification that the medication for the order has been prepared with the appropriate components. Upon verification, the virtual queue is updated to reflect that the order has been filled and that the prepared medication for the order may be retrieved for delivery to a patient.

Turning now to the drawings, FIG. 1 illustrates an example architecture 100 for managing preparation of a medication according to certain aspects of the present disclosure. For ease and clarity of illustration only, without any intent to limit the scope of the present disclosure any way, it is assumed that the prepared medication provided as an example for FIG. 1 is an anesthetic IV solution.

The architecture 100 includes a pharmacy 1 having a medication storage area 10, a fill and/or preparation (fill/prep) area 20, and a delivery pickup area 30 (e.g., bin-sorting area). The medication storage area 10 includes a plurality of medications and supplies including, for example, an anesthetic drug (e.g., bupivacaine or chloroprocaine) and an appropriate fluid for the anesthetic drug. The anesthetic drug and the fluid are taken from the medication storage area 10 to the prep/fill area 20 where they are mixed together to produce the anesthetic IV solution. A patient/medication ID device 72, such as a barcode label or a radio frequency identification (RFID) tag, is provided on (e.g., affixed to) a package 70 (e.g., IV bag) containing the IV solution at the prep/fill area 20. The patient/medication ID device 72 includes patient/medication ID information indicative of the medication and the patient to whom the medication is prescribed. The package 70 is then taken by a technician at the pharmacy 1 to the delivery pickup area 30. The technician determines an appropriate bin or delivery cart 90 into which to place the package 70, and then loads the package 70 onto the appropriate delivery cart 90 for delivery to a scheduled delivery/drop location 60 (e.g., a patient room) by a delivery person 2.

In the illustrated embodiment, the prep/fill area 20 has a barcode reader 24 provided therein that the technician at the pharmacy 1 can use to read the patient/medication ID device 72 (a barcode label in the illustrated example) before the package 70 is taken to the delivery pickup area 30. The prep/fill area 20 may also have an image recording device 25, such as a camera, for recording preparation of the package 70. The delivery pickup area 30 has a barcode reader 34 connected to a client 110 provided therein that the technician at the pharmacy 1 can use to read the patient/medication ID device 72 once the package 70 is taken to the delivery pickup area 30. The delivery cart 90 may also be provided with a location barcode label reader. The delivery person 2 can use the barcode reader 34 to scan the package 70 to indicate the delivery person 2 will begin delivery of the package 70.

The pharmacy 1 includes a server 130 (e.g., pharmacy server) that includes a processor 40. The server 130 is coupled to an output device 134, such as a display, and an input device 136, such as a keyboard. The server 130 can be any device having an appropriate processor, memory, and communications capability for running a preparation tracking application and receiving, processing, and sending information associated with a medication database 45 and prepared medications. The processor 40 is coupled to the medication database 45 that is configured to store a variety of information. The medication database 45 can include information such as, but not limited to: the patient's name or ID, the medication name or ID, the scheduled delivery location 60, the scheduled delivery time, an expiration date or time for a prepared medication, an estimated administration time for the prepared medication, an urgency of delivery of the prepared medication, a current location of the prepared medication, an order status of the prepared medication, a return status of the prepared medication, one or more read locations where the medication/patient ID information and/or the location ID information was read by the barcode scanner 84, a time when the information was read, and the name or ID of the delivery person 2. The medication database 45 is configured to electronically provide and receive the information according to various interoperability standards, such as the HL7 standard, which can include data received from various medical devices such as an infusion pump. The electronic data feed providing the HL7 standardized data is different than a printer feed in which data is not provided for exchange, integration, sharing, and retrieval of electronic health information as with the HL7 standardized data. For example, the electronic data feed can include data formatted for the HL7 standard that indicates a current or past status of an infusion pump, respiratory device, dispensing machine, or other medical device.

The processor 40 of the server 130 at the pharmacy 1 is configured to electronically receive information from the medication database 45 according to an interoperable standard such as the HL7 standard and process the information to identify one or many orders to be prepared in the prep/fill area 20 of the pharmacy 1. The processor 40 then determines whether each order can be filled using an available medication that has already been prepared (e.g., in the medication storage area 10), a retrieved or retrievable medication that will no longer be needed by another patient, or whether the order must be filled by preparing a new medication. As such, the processor 40 is configured to make the determinations in "real-time," namely, substantially immediately in response to corresponding data from the medication database 45.

A medication may be retrieved by the delivery person 2 and returned to the pharmacy 1. The retrieved medication may be scanned upon its return to the pharmacy 1 and listed in an inventory of available retrieved medications. In certain aspects, the retrieved medication may be scanned when initially retrieved (e.g., but not yet returned to the pharmacy 1) by the delivery person 2 and also be listed in the inventory of available solutions. If the retrieved medication has passed its expiration date, or is not within a threshold time duration of its expiration date, e.g., exceeding the amount of time required to deliver to and administer the retrieved medication at another location, then the retrieved medication is discarded. However, if the retrieved medication is not within the threshold time duration of its expiration date, the retrieved medication is re-entered into inventory for possible re-use.

The processor 40 of the server 130 at the pharmacy 1 provides appropriate notifications to an output device 134 based on the determination whether each order can be filled using an available medication that has already been prepared, a retrieved or retrievable medication that will no longer be needed by another patient, or whether the order must be filled by preparing a new medication, including, for example, how the order should be filled, and a location of a retrievable medication that can be used to fill the order. For example, a notification can be displayed on the output device 134 indicating that a retrieved medication for bupivacaine IV solution and be used to fill a new order for bupivacaine IV solution. In determining whether retrieved or retrievable medication can be used to fill the order, the processor 40 is configured to calculate the expiration date of the retrieved or retrievable medication. The expiration date of the retrieved or retrievable medication is used to determine whether the retrieved or retrievable medication can be used to fill the order.

The processor 40 is configured to determine an expiration date for a returned package 70 based on, for example, the stability and sterility of the returned package 70. Information indicative of the stability and sterility of the returned package 70 may be obtained from the medication database 45. For example, the stability of the returned package 70, which indicates a length of time a drug in the returned package 70 retains its properties without loss of potency (i.e., "shelf life") can initially be entered by a pharmacist or other health care provider when the returned package 70 is first prepared. The sterility of the returned package, which indicates the conditions in which the package 70 was prepared (e.g., an environment particle count), can be determined based on a known location in which the package 70 was prepared as stored in the medication database 45. For instance, if the package returned package 70 is prepared in a sterile zone, it may be given a longer expiration time frame than if the returned package 70 were not prepared in a sterile zone. The processor 40, based on a stability date entered by a pharmacist and a sterility indicator calculated based on the known location in which the package 70 was prepared, can then generate an expiration date for the returned package 70.

In certain aspects where a retrieved or retrievable medication can be used to fill the order, an identification of the retrievable medication and of the retrieval location 50 can be provided to a client 110 in or associated with the delivery pickup area 30 for display on an output device 114 at or near the delivery pickup area 30 instructing the delivery person 2 to retrieve the retrievable medication from the retrieval location 50. A route for retrieving the retrievable medication from the retrieval location 50 (e.g., a patient room) may also be provided to the client 110 based on, for example, current deliveries being made by the delivery person 2. The client 110 can be, for example, a computer system associated with the delivery pickup area 30 such as a desktop computer or mobile computer. The client 110 can also be, for example, a tablet computer, mobile device (e.g., a smartphone or PDA), or any other device having appropriate processor, memory, and communications capabilities. A client 110 that is a mobile device may, for example, be associated with the delivery person 2.

Upon determining how the order from the medication database 45 can be filled, the processor 40 of the server 130 in the pharmacy 1 provides an entry for the order for display on the output device 134 of the server 130 and in a virtual queue of orders to be filled by the pharmacy 1. The entry for the order is listed at an appropriate position in the queue among any other order(s) in the queue. The position of each order for a medication in the queue as determined by the processor 40 may be based on, for example, an estimated amount of time to prepare the medication, an estimated amount of time to deliver the medication to the delivery/drop location 60, an estimated time at which the medication will be needed for administration to a patient at the delivery/drop location 60, a delivery deadline for the medication, a degree of urgency for delivery of the medication, a type of the medication, or a component of the medication. Two or more medication orders that require the same or similar medication components may be grouped together in the queue, for example, to avoid unnecessary wasting of the component used to prepare the medication.

Records of the preparation of the medication for the order using one or more components is recorded and stored in the medication database 45 for later verification by a pharmacist or other inspector responsible for authorizing the prepared medication as being ready for delivery to a patient. The records can include, for example, images or video recorded by the image recording device 25 or barcodes for the component(s) read by the barcode reader 24. The records may then be provided to the pharmacist for verification. Upon verification, the package 70 prepared for the order is identified as prepared in the queue and ready for delivery to the delivery/drop location 60 by the delivery person 2. At any time, if the medication database 45 indicates that the order has changed, such as due to a status change of the patient for whom the order is written, the queue is automatically updated to modify or remove the listing for the order in the queue based on the change to the order indicated by the medication database 45.

The delivery location 60 and/or the retrieval location 50 can include, for example, patient rooms having an infusion device for providing an IV infusion from a package to a patient. In the illustrated example, the retrieval location 50 and the delivery location 60 are provided with location barcode label 52 and location barcode label 62, respectively. Each of the location barcode labels 52, 62 includes unique location ID information indicative of the respective location 50, 60 where the corresponding barcode label is provided. As described above, the package 70 (e.g., IV bag) containing the medication (e.g., IV solution) is provided with a patient/medication identification (ID) device 72. In the illustrated example, the patient/medication ID device 72 is a barcode label that includes patient/medication information indicative of the patient (e.g., "Jane Smith") and the medication (e.g., "bupivacaine IV solution"). The patient/medication information may also contain other drug or patient related information such as the patient's medical conditions (e.g., allergies), name of the drug (e.g., bupivacaine), the drug dosage, the drug concentration, the drug administration schedules, and the drug administration rate.

Also depicted in the architecture 100 of FIG. 1 is a reader device 84 that is hand carried by the delivery person 2 and/or attached to the delivery cart 90 and is configured to read the patient/medication information from the patient/medication ID device 72 provided on the package 70. In the illustrated example, the reader device 84 is a barcode scanner. In those embodiments in which the barcode scanner 84 is hand carried by the delivery person 2, the scanner 84 is also configured to read the location ID information from the location barcode labels 52, 62, 92.

In the embodiments described above, the location ID devices 52, 62, 92 and/or the patient/medication ID device 72 are passive ID devices, meaning that certain action (e.g., scanning) has to be taken by the participant (e.g., a pharmacy technician or the delivery person 2) to retrieve information therefrom. In other embodiments, the ID devices can be active ID devices, meaning that the information retrieval from the ID devices occur automatically without an action taken by the participant. In some embodiments, the active ID devices can actively transmit signals containing the relevant information to the reader device 84 through a wireless link. The wireless link can use a variety of technologies including Bluetooth, ZigBee, wireless USB, and proprietary systems. In other embodiments, the active ID devices do not themselves transmit signals, but respond to query signals generated by a reader device (e.g., by altering impedance of an RF circuit therein) as the reader device passes by the ID devices in close proximity.

In the illustrated example, each time the barcode scanner 84 scans an ID device (e.g., patient/medication ID device or location ID device), the information read thereby is provided to the medication database 45 via wireless transmission to a wireless bridge 50 that receives the information. The bridge 50 is in data communication with the processor 40 via a hospital network 150. The network 150 can include, for example, any one or more of a personal area network (PAN), a local area network (LAN), a campus area network (CAN), a metropolitan area network (MAN), a wide area network (WAN), a broadband network (BBN), the Internet, and the like. Further, the network 150 can include, but is not limited to, any one or more of the following network topologies, including a bus network, a star network, a ring network, a mesh network, a star-bus network, tree or hierarchical network, and the like.

The processor 40 is configured to receive medication/patient ID information and/or location ID information read by the barcode scanner 84, generate location, use, and re-use information therefrom. The processor 40 is configured to store the information in the medication database 45.

The architecture 100 further comprises tracking devices 120, 152 that allow a care provider 4 (e.g., a nurse assigned the task of administering the patient-specific medication to the patient) to monitor the progress of the delivery of the medication. Each of the tracking devices 120, 152 is configured to receive a tracking request by the care provider 4, access the medication database 45, either directly or via the processor 40, retrieve the delivery progress information stored in the database 45, and indicate a delivery progress of the medication to the care provider 4 based on the delivery progress information. In the illustrated example, the tracking device 120 is an automated dispensing machine having a processor (not shown), a display 121, and a keyboard 123; and the tracking device 152 is a mobile communication device (e.g., a cell phone, personal digital assistant (PDA), or pager) having a processor (not shown), a display 151, and a keyboard 153. The delivery progress information can inform the care provider 4 of a last-known read location and time of the last reading. Based on such information, the care provider 4 can decide, e.g., whether to wait for the delivery at the delivery location 60, go to the delivery location later at an expected delivery time, or go to the last-known location to retrieve the medication from the cart 90.

Figure 2:
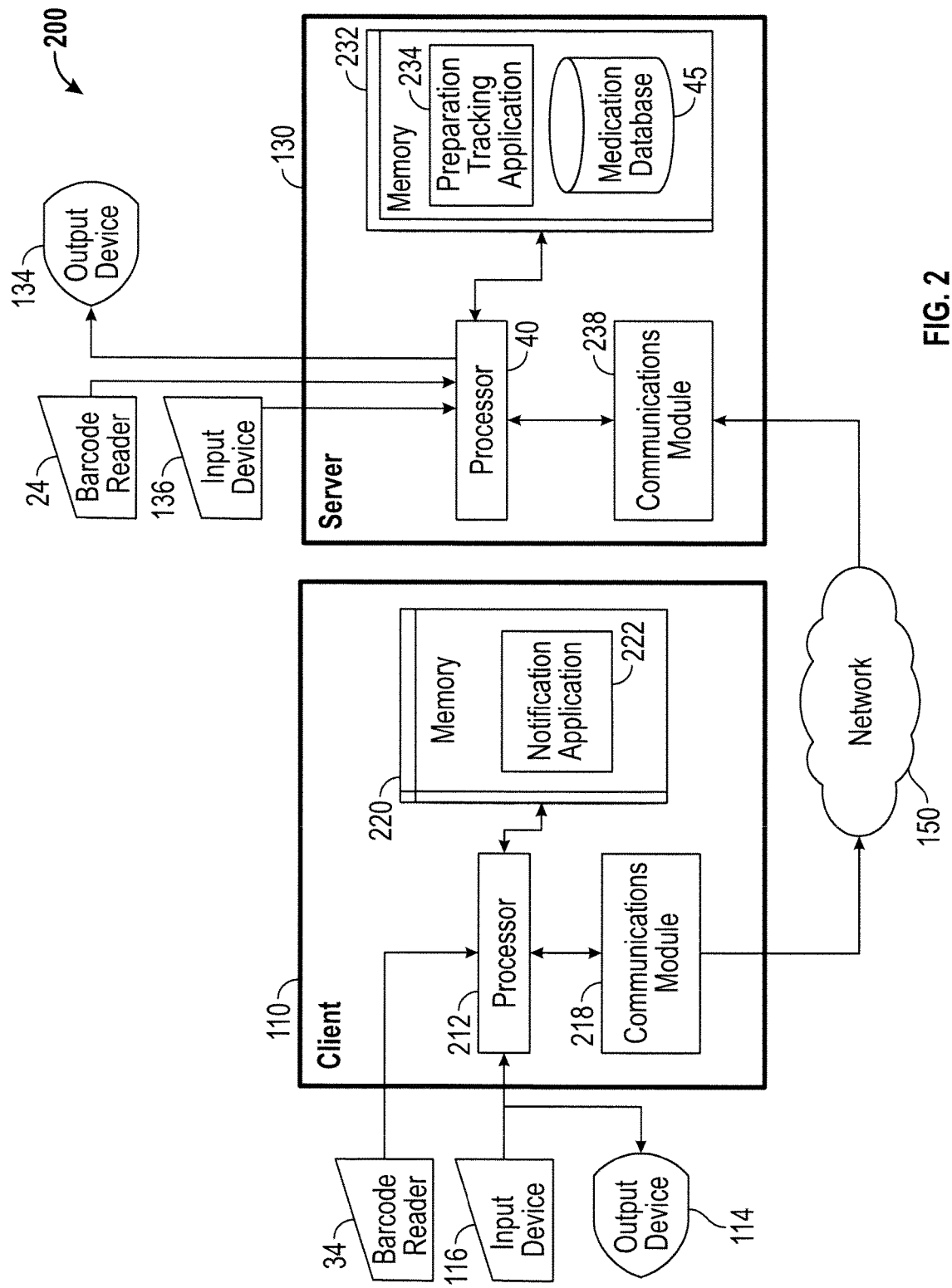
FIG. 2 is a block diagram illustrating an example client and server from the architecture of FIG. 1 according to certain aspects of the disclosure.

FIG. 2 is a block diagram 200 illustrating an example server 130 and client 110 in the architecture 100 of FIG. 1 according to certain aspects of the disclosure. The client 110 and the server 130 are connected over the network 150 via respective communications modules 218 and 238. The communications modules 218 and 238 are configured to interface with the network 150 to send and receive information, such as data, requests, responses, and commands to other devices on the network 150. The communications modules 218 and 238 can be, for example, modems or Ethernet cards.

The server 130 includes a processor 40, a communications module 238, and a memory 232 that includes the medication database 45 and a preparation tracking application 234. The processor 40 of the server 130 is configured to execute instructions, such as instructions physically coded into the processor 40, instructions received from software in memory 240, or a combination of both. For example, the processor 40 of the server 130 executes instructions from the preparation tracking application 234 to receive information indicative of an order for medication for a patient from an electronic data feed (e.g., medication database 45) and determine whether the order can be filled with an available prepared medication or a returned medication.

A determination whether an available prepared or returned medication can be used to fill the order can be based on, for example, a comparison between at least two of an expiration time of the available prepared or returned medication, an estimated amount of time for delivering the available prepared or returned medication to the delivery/drop location 60, an estimated time at which the available prepared or returned medication will be administered to a patient at the deliver/drop location 60, and a delivery deadline for the available prepared or returned medication.

For example, if a returned medication is estimated to expire in ten minutes, and it is estimated to take thirty minutes to deliver the returned medication to the delivery/drop location 60, then the determination may indicate that the returned medication cannot be used for completing the order of the other medication. As another example, if the order must be delivered to the delivery/drop location 60 within two hours, and the estimated time to deliver an available prepared medication to the delivery/drop location 60 is one hour, then the determination may indicate that the available prepared medication should be used for completing the order. As yet another example, if a returned medication is estimated to expire in one hour, it is estimated to take thirty minutes to deliver the returned medication to the delivery/drop location 60, and the order must be delivered to the delivery/drop location 60 within forty-five minutes, then the determination may indicate that the returned medication can be used for completing the order of the other medication.

When the processor 40 determines the order can be filled with an available prepared medication or a returned medication, the processor 40 is configured to provide a notification to fill the order with the available prepared medication or returned medication. The notification can include, for example, an instruction to assist with preparation of the order using the prepared or returned medication. For instance, the notification can indicate that a returned medication should be combined with another returned medication to fill the order, and further indicate a pickup location (e.g., retrieval location 50) at which the medication can be retrieved if it is not yet retrieved. As an example, if two returned medications are each for Cefazolin (2 gm/NS 50 ml), and a new order for Cefazolin (4 gm/NS 100 ml) is received by the processor 40, then the processor 40 can send a notification (e.g., to the output device 134) indicating that the two returned medications of Cefazolin (2 gm/NS 50 ml) should be combined to fill the new order for Cefazolin (4 gm/NS 100 ml).

Similarly, the processor 40 may be configured to provide a notification indicating to proceed with completing the order when the determination indicates that a prepared or returned medication is not available for completing the order. For example, if the order for the medication must be delivered to the delivery/drop location 60 within thirty minutes, and the estimated time to deliver a returned medication to the delivery/drop location 60 is one hour, then a notification on the output device 134 can indicate that the returned medication cannot be used for completing the order of the other medication. In certain aspects, the same notification or another notification can be provided by the processor 40 indicating the returned medication is expired, or the returned medication will expire within a threshold time period. The threshold time period may be based on an expiration time of the returned medication and an estimated amount of time for delivering the returned medication to the delivery/drop location 60.

The processor 40 is further configured to place the order in a virtual queue of orders to be filled. The order for medication from the medication database 45 is placed in a position in the virtual queue determined based on various factors. The factors affecting the position of an order for medication in the virtual queue include, for example, an estimated amount of time to prepare the medication, an estimated amount of time to deliver the medication to a delivery location (e.g., delivery/drop location 50), an estimated time at which the medication will be needed for administration to a patient at the delivery location, a delivery deadline for the medication, a degree of urgency for delivery of the medication, a type of the medication, or a component of the medication.

The order may be listed by the processor 40 at a position among other orders in the virtual queue where the order is provided with other orders of the same type (e.g., the same type of medication) or having a shared component. For instance, a new order for medication that requires a particular medication component for formulation can be grouped with other orders in the virtual queue that require the same particular medication component for formulation.

Such component based aggregation of medication orders may allow a healthcare facility, such as a hospital, to substantially minimize the amount of medication that is wasted when component medications are picked, or retrieved, by a healthcare professional, for the purposes of preparing ordered medications. For example, the processor 40 may provide, to a healthcare professional and for display on the output device 134, an indication of a container, or a set of containers, which provides a sufficient amount of the component medication to prepare the orders while minimizing any excess amount of the component medication, e.g. any amount of the component medication that is left unused after the ordered medications are prepared. The processor 40 thus minimizes the amount of component medications that is wasted when ordered medications are prepared. For example, the processor 40 may aggregate medication orders based on common component medications such that a healthcare professional can sequentially prepare ordered medications that have a common component medication. In this manner, the likelihood of any component medication being wasted, or expiring, is substantially minimized.

Accordingly, the processor 40 is configured to aggregate received orders into batches, or groups, e.g. based on the component medications that are indicated by each order for display in the queue. For example, the processor 40 may batch the orders such that orders that have a common (e.g., the same) component medication are picked together. After batching the orders, e.g. based on the component medications, the processor 40 may select the first batch of orders and determine the containers from inventory (e.g., in the medication storage area 10) that should be picked to prepare the first batch of orders in a manner that minimizes wasted component medications. The containers may include vials, bags, bottles, packages, or generally any container that can store a component medication.

The processor 40 of the server 130 is further configured to execute instructions from the preparation tracking application 234 to determine a first batch of orders and provide an indication of the component medications needed to prepare the first batch, the amount of the component medications that needs to be retrieved for the first batch, and the containers from inventory that should be retrieved for the first batch. For example, the processor 40 may provide a user interface for display on the output device 134 to assist a healthcare professional with picking the component medications for the first batch. The healthcare professional may retrieve the containers from the inventory of the medication storage area 10 for preparing the first batch. For example, the healthcare professional may identify each container that is retrieved from inventory, e.g. by scanning the containers with a bar code scanner 24. The processor 40 may transmit indications of the scanned containers to medication database 45 and the medication database 45 may store an indication that the containers are being removed from the inventory of the medication storage area 10 and being delivered to a temporary inventory of the preparation/fill area 20. The containers may then be delivered to the preparation/fill area 20 for preparation of the first batch of orders.

The processor 40 of the server 130 is further configured to execute instructions from the preparation tracking application 234 to receive an image or barcode identifying a component used to formulate the medication, and provide the image or barcode to a person, such as the pharmacist, responsible for verifying the medication is filled using the component. For example, during preparation of the package 70, a technician may place each component medication used to formulate the package 70 into a capture area of the prep/fill area 20 where the image recording device 25 or barcode reader 24 can capture a record (e.g., image or barcode reading) of each component medication being used. The processor 40 is configured to receive an input indicating the person has verified the medication has been filled using the component, and provide an indication that the order for the medication is ready for delivery to the patient. For example, the image or barcode reading of each component medication used to formulate the package 70 can be provided to a pharmacist in the pharmacy 1 or remote from the pharmacy 1 for review (e.g., as displayed on output device 134) and verification (e.g., using an input device 136 of the server 130) that the appropriate component medications were used to prepare the package 70. Upon verification by the pharmacist, the processor 40 indicates that the order is complete and that the package 70 for the order is ready for delivery.

Figure 3:
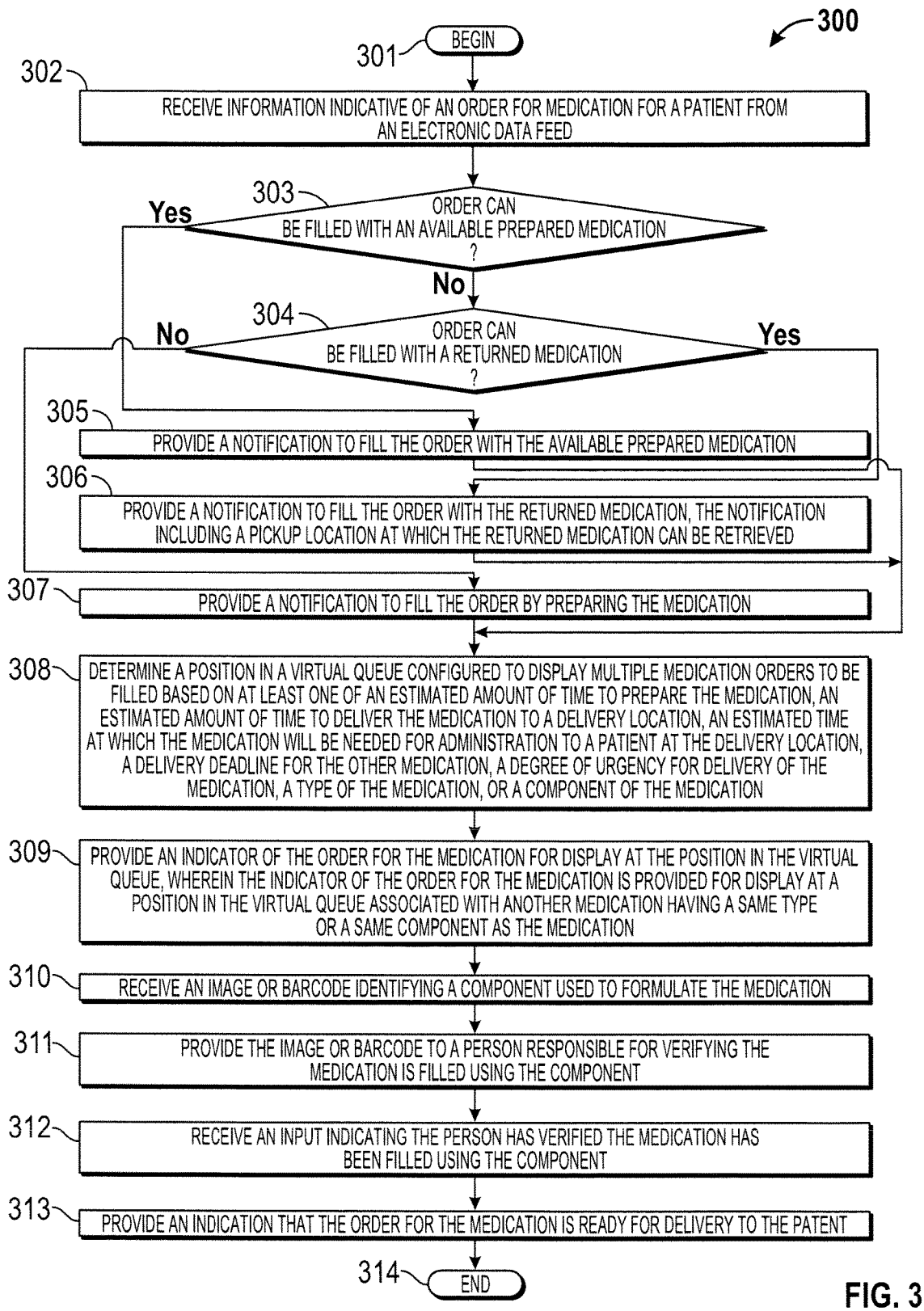
FIG. 3 illustrates an example process for managing preparation of a medication using the server of FIG. 2.

FIG. 3 illustrates an example process 300 for managing preparation of a medication using the example server 130 of FIG. 2. While FIG. 3 is described with reference to FIG. 2, it should be noted that the process steps of FIG. 3 may be performed by other systems. The process 300 begins by proceeding from beginning step 301 when the preparation tracking application 234 is initiated to step 302 when information indicative of an order for medication for a patient is received from an electronic data feed. Next, in decision step 303, a determination is made whether the order can be filled with an available prepared medication. If the determination of step 303 indicates that the order can be filled with an available prepared medication, the process 300 proceeds to step 305 in which a notification is provided to fill the order with the available prepared medication. If the determination of step 303 indicates that a prepared medication is not available that can be used to fill the order, the process 300 proceeds to decision step 304 in which a determination is made whether the order can be filled with a returned medication.

If in decision step 304 it is determined that the order can be filled with a returned medication, the process 300 proceeds to step 306 in which a notification to fill the order with the returned medication is provided. The notification may include a pickup location (e.g., retrieval location 50) at which the returned medication can be retrieved. If in decision step 304 it is determined a returned medication cannot be used to fill the order, the process 300 proceeds to step 307 in which a notification to fill the order by preparing the medication is provided.

Next, after steps 305, 306, or 307, the process 300 proceeds to step 308 in which a position in a virtual queue configured to display multiple medication orders to be filled is determined based on at least one of many factors. The factors include an estimated amount of time to prepare the medication, an estimated amount of time to deliver the medication to a delivery location, an estimated time at which the medication will be needed for administration to a patient at the delivery location, a delivery deadline for the medication, a degree of urgency for delivery of the medication, a type of the medication, or a component of the medication. In step 309, an indicator of the order for the medication is provided for display (e.g., on the output device 134) at the determined position in the virtual queue. The indicator of the order for the medication can be provided for display at a position in the virtual queue associated with another medication having a same type or a same component as the medication (e.g., as a grouping of medications of the same type or having the same component).

Next, in step 310, an image or barcode is received identifying a component used to formulate the medication, and in step 311 the image or barcode is provided to a person, such as a pharmacist, responsible for verifying the medication is filled using the component. After receiving an input (e.g., using input device 136 of the server 130) in step 312 indicating the person has verified the medication has been filled using the component, the process 300 proceeds to step 313 in which an indication that the order for the medication is ready for delivery to the patient is provided. The indication can be provided for display with the virtual queue displayed on the output device 134, or can be provided for display on the output device 114 of the client 110. The process 300 then ends in step 314.

FIG. 3 set forth an example process 300 for managing preparation of a medication using the example client 110 and server 130 of FIG. 2. An example will now be described using the example process 300 of FIG. 3, a server 130 that is a desktop computer, a client 110 that is a tablet associated with a delivery person 2, and a new order to be filled for Cefazolin (2 gm/NS 50 ml).

The process 300 begins by proceeding from beginning step 301 when the preparation tracking application 234 is initiated to step 302 when a new order for Cefazolin (2 gm/NS 50 ml) for a patient in room 5E-12 (i.e., the delivery/drop location 60) is received from a hospital's HL7 feed. Next, in decision step 303, a determination is made whether the order for Cefazolin (2 gm/NS 50 ml) can be filled with any available prepared medication. The determination of step 303 indicates that a prepared medication is not available that can be used to fill the order for Cefazolin (2 gm/NS 50 ml), and the process 300 proceeds to decision step 304 in which a determination is made whether the order for Cefazolin (2 gm/NS 50 ml) can be filled with a returned medication. In decision step 304 it is determined that the order for Cefazolin (2 gm/NS 50 ml) can be filled with a returned medication, so the process 300 proceeds to step 306 in which a notification to fill the order with the returned medication is provided for display.

Figure 4A:
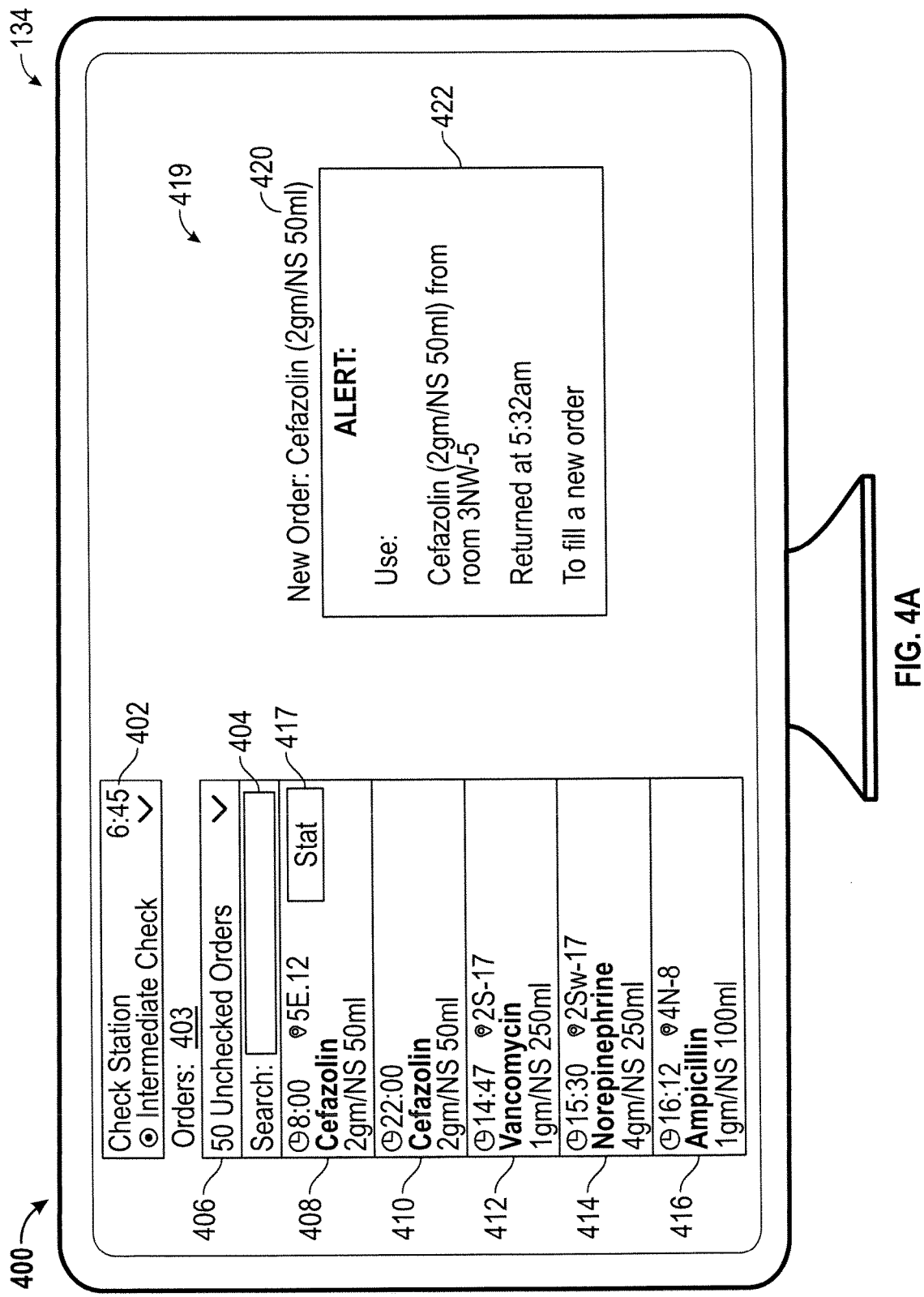

Next, after step 306, the process 300 proceeds to step 308 in which a position in a virtual queue configured to display multiple medication orders to be filled is determined based on at least one of many factors. The factors include an estimated amount of time to prepare the medication, an estimated amount of time to deliver the medication to a delivery location, an estimated time at which the medication will be needed for administration to a patient at the delivery location, a delivery deadline for the medication, a degree of urgency for delivery of the medication, a type of the medication, or a component of the medication. In step 309, an indicator of the order for the medication is provided for display (e.g., on the output device 134) at the determined position in the virtual queue as provided in the example illustration 400 of FIG. 4A. Specifically, FIG. 4A provides an example illustration 400 of a graphical user interface for displaying the virtual queue 403 and notifications 420 and 422 on the output device 134 of the pharmacy's desktop computer 130. The graphical user interface includes an identification of the current time 402, 6:45 AM, and a virtual queue 403 of 50 unchecked orders 406 to be filled that may be sorted by, for example, priority, due time, location, type, medication component, or alphabetically, and may be searched using a search interface 404. Five orders 408, 410, 412, 414, and 416 are listed and additional orders may be viewed by scrolling the interface below the five listed orders 408, 410, 412, 414, and 416.

For each order, a due time, patient location, medication information, level of priority, and return status may be indicated. For example, the first order listed identifies the new order 408 for Cefazolin (2 gm/NS 50 ml) received in step 302 that is to be delivered to patient room 5E-12 by 8:00 AM. The indicator of the new order 408 for Cefazolin (2 gm/NS 50 ml) is provided at a first position in the virtual queue 403 because of the delivery deadline of 8:00 AM for the medication and the degree of urgency indicated as stat for delivery of the medication. The indicator of the new order 408 for Cefazolin (2 gm/NS 50 ml) is provided in the first position next to the other order 410 for Cefazolin (2 gm/NS 50 ml), which is in the second position. The two orders 408 and 410 are grouped together because they are medications that share medication components. If one of the two orders 408 or 410 is selected, a second user interface 430 may be displayed as provided in the example illustration of FIG. 4B.

The example user interface 430 includes an information display area 431, and a batch display area 432. The information display area 431 may display information regarding a selected order for a medication and/or a selected component medication. The batch display area 432 may display batches of orders for medications that have been grouped together, e.g., based on a common component medication. In operation, the user interface 430 may be displayed on the output device 134 in the pharmacy 2 and particularly in the medication storage area 10, e.g. to facilitate a healthcare professional with picking component medications in a manner that minimizes any wasted amounts of the component medications.

Returning to the example illustration 400 of FIG. 4A, the user interface also includes a messages area 418 that identifies 420 the new order for Cefazolin (2 gm/NS 50 ml) received in step 302, but also includes the notification 422 of step 306 to be read by the pharmacist filling the new order for Cefazolin (2 gm/NS 50 ml). The notification 422 indicates to the pharmacist that an order for Cefazolin (2 gm/NS 50 ml) that has been returned from patient room 3NW-5 at 5:32 AM may be used to fill the new order 408 for Cefazolin (2 gm/NS 50 ml).

In certain aspects where an already prepared but discontinued order is retrievable to fill the new order for Cefazolin (2 gm/NS 50 ml) received in step 302 but not yet retrieved, the pharmacy's desktop computer 130 may provide another notification to the tablet 110 of a delivery person 2 who is responsible for delivering and retrieving medications, such as infusion solutions, within a healthcare facility so that the delivery person 2 can retrieve the medication to fill the new order for Cefazolin (2 gm/NS 50 ml). The delivery person 2 may thus be provided with a list of discontinued medications and their location in healthcare facility on their tablet 110. The list of discontinued medications provided to the tablet 110 of the delivery person 2 can be ordered, for example, to identify an efficient route (e.g., based on distance, an urgency of retrieving a medication, etc.) for retrieving discontinued medications. In certain aspects, if the delivery person is delivering medications to a particular area of the healthcare facility, then the list of discontinued medications can be ordered based on the areas to which the delivery person 2 is delivering. The delivery person 2 may then retrieve the discontinued medications and return them to a workroom in the pharmacy.

Figure 4C:
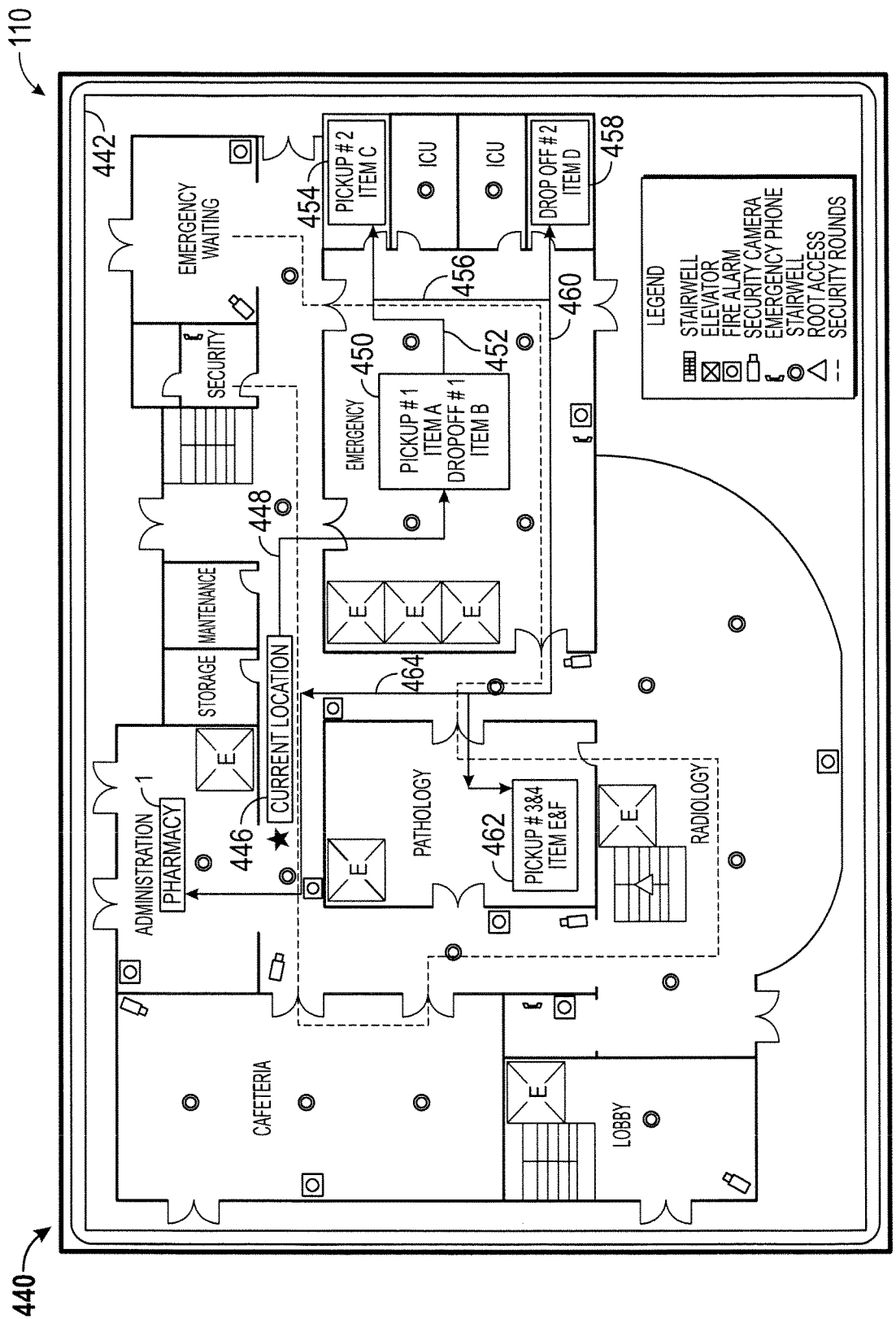

FIG. 4C provides an example illustration 440 of the tablet 110 displaying an efficient route for retrieving discontinued medications. Specifically, the tablet 110 displays a visualization 442 of a route by which to retrieve four unused medications and deliver two new medications. The visualization indicates a current location 446 of the tablet device 110 and the route, from the current location 446, to retrieve four unused medications and deliver two new medications. From the current location 446, the route proceeds 448 to a first location 450 in which one medication is picked up and one medication is dropped off. Next, the route proceeds 452 to a second location 454 in which a medication is picked up. Thereafter, the route proceeds 456 to a third location 458 in which a medication is dropped off. Afterwards, the route proceeds 460 to a fourth location 462 in which two medications are picked up. The route then returns 464 to the pharmacy 1 so that the four retrieved unused medications can be returned.

Figure 4D:
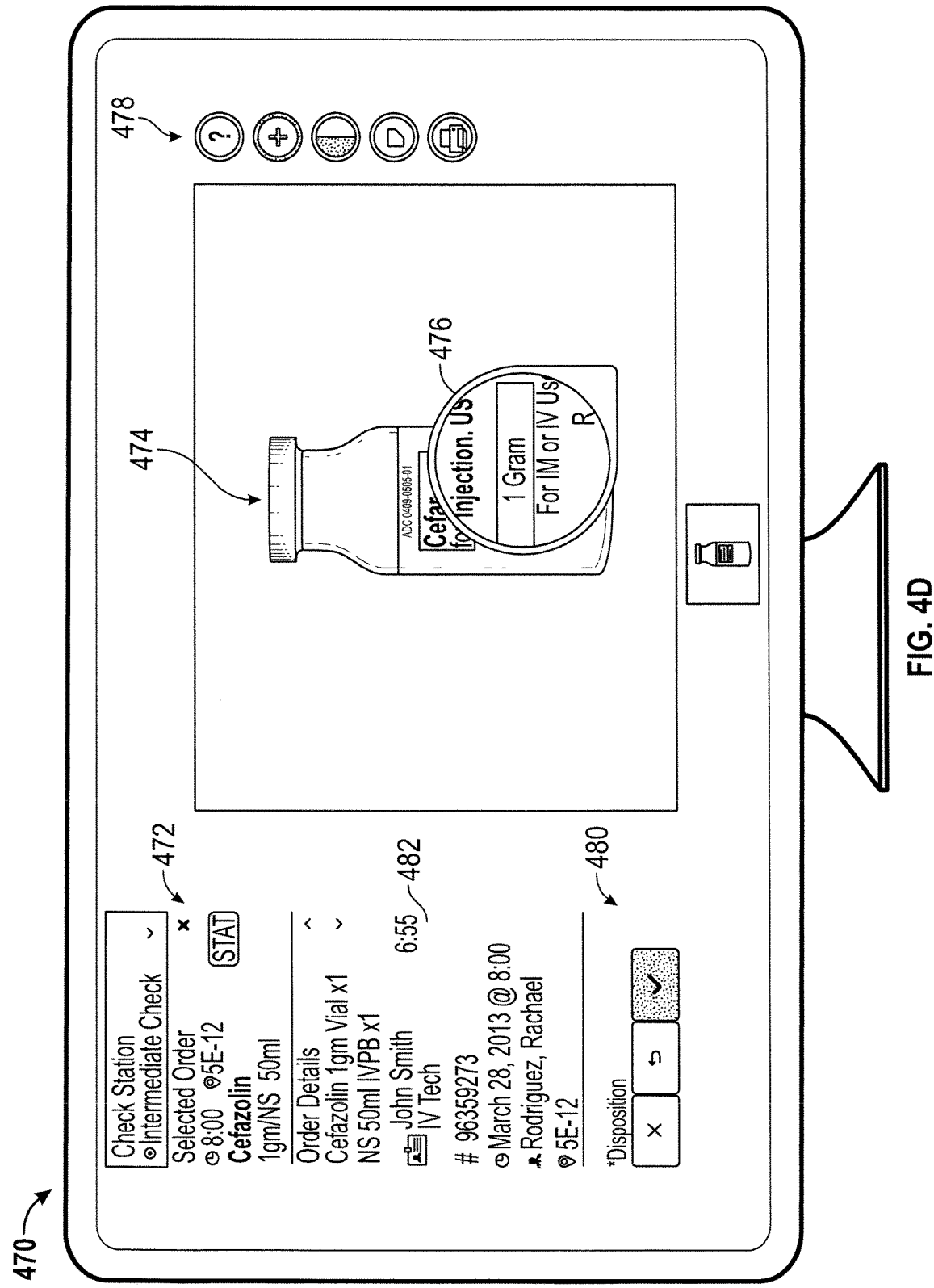

Returning to the process 300 of FIG. 3, in step 310, an image or barcode is received identifying a component used to formulate the new order 408 of Cefazolin (2 gm/NS 50 ml). In step 311 the image or barcode is provided to the pharmacist to verify the new order 408 for Cefazolin (2 gm/NS 50 ml) is filled using the correct medication component as provided in the example illustration 470 of FIG. 4D. The example illustration includes a graphical user interface that identifies details of the order being filled 472. The details 472 include the medication components used to prepare the medication. The graphical user interface also includes an identification of the patient for whom the medication is being prepared, as well as the person (e.g., pharmacy technician) preparing the medication 482. The graphical user interface further includes an image 472, taken by the person preparing the medication, of each component medication used to formulate the medication to fill the order, as well as a magnification 472 following a cursor of the input device 136 to assist the pharmacist in verifying each medication component. Graphical tools 478 are provided to assist the pharmacist in viewing the image 474, including zoom, contrast, photo annotation, and label reprinting. The pharmacist verifies each medication component as correct for formulating the order using a disposition toolbar 480 provided in the graphical user interface.

After receiving an input (e.g., using input device 136 of the server 130) in step 312 indicating the pharmacist has verified the medication has been filled using the medication component, the process 300 proceeds to step 313 in which an indication that the order for the medication is ready for delivery to the patient is provided. The indication can be provided for display with the virtual queue displayed on the output device 134, or can be provided for display on the output device 114 of the client 110. The process 300 then ends in step 314.

Figure 5:
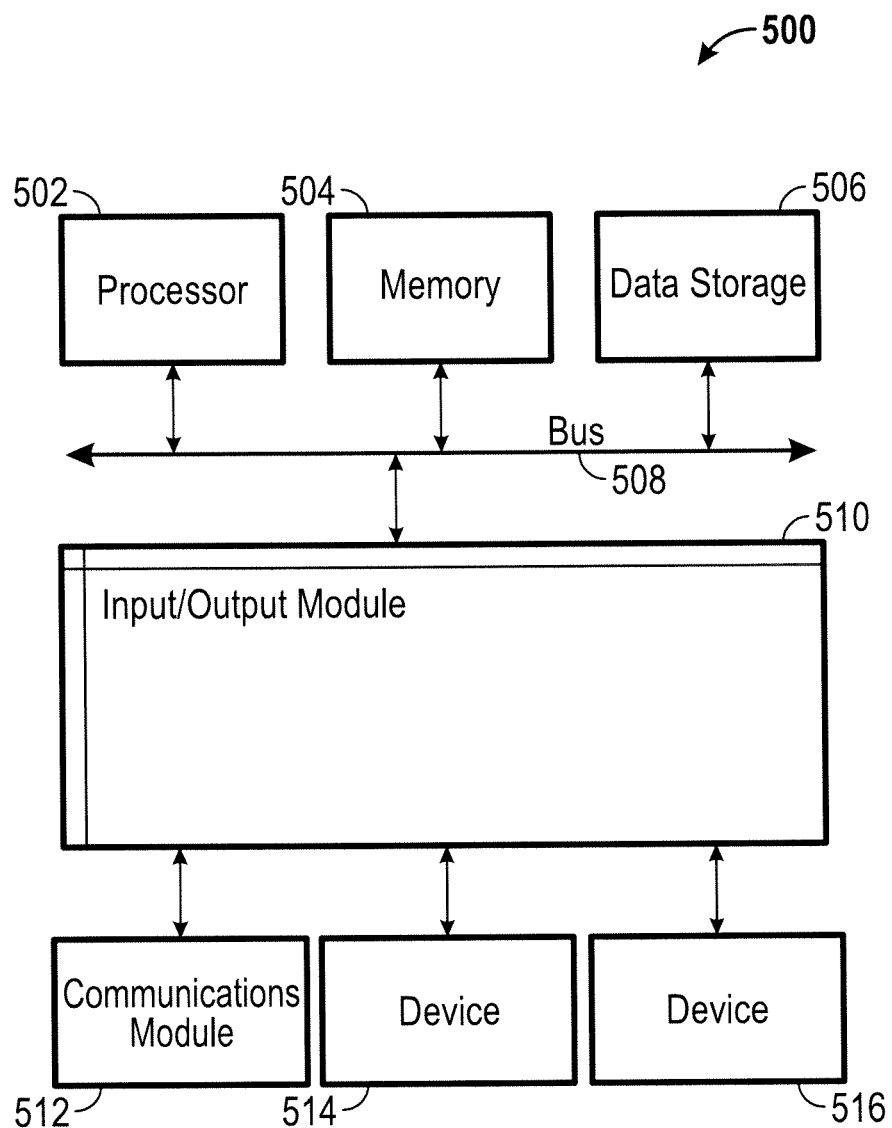
FIG. 5 is a block diagram illustrating an example computer system with which the client and server of FIG. 2 can be implemented.

FIG. 5 is a block diagram illustrating an example computer system 500 with which the client 110 and server 130 of FIG. 2 can be implemented. In certain aspects, the computer system 500 may be implemented using hardware or a combination of software and hardware, either in a dedicated server, or integrated into another entity, or distributed across multiple entities.

Computer system 500 (e.g., client 110 and server 130) includes a bus 508 or other communication mechanism for communicating information, and a processor 502 (e.g., processor 212 of client 110 and processor 40 of server 130) coupled with bus 508 for processing information. By way of example, the computer system 500 may be implemented with one or more processors 502. Processor 502 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable entity that can perform calculations or other manipulations of information.

Computer system 500 can include, in addition to hardware, code that creates an execution environment for the computer program in question, e.g., code that constitutes processor firmware, a protocol stack, a database management system, an operating system, or a combination of one or more of them stored in an included memory 504 (e.g., memory 220 of client 110 and memory 232 of server 130), such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device, coupled to bus 508 for storing information and instructions to be executed by processor 502. The processor 502 and the memory 504 can be supplemented by, or incorporated in, special purpose logic circuitry.

The instructions may be stored in the memory 504 and implemented in one or more computer program products, i.e., one or more modules of computer program instructions encoded on a computer readable medium for execution by, or to control the operation of, the computer system 500, and according to any method well known to those of skill in the art, including, but not limited to, computer languages such as data-oriented languages (e.g., SQL, dBase), system languages (e.g., C, Objective-C, C++, Assembly), architectural languages (e.g., Java, .NET), and application languages (e.g., PHP, Ruby, Perl, Python). Instructions may also be implemented in computer languages such as array languages, aspect-oriented languages, assembly languages, authoring languages, command line interface languages, compiled languages, concurrent languages, curly-bracket languages, dataflow languages, data-structured languages, declarative languages, esoteric languages, extension languages, fourth-generation languages, functional languages, interactive mode languages, interpreted languages, iterative languages, list-based languages, little languages, logic-based languages, machine languages, macro languages, metaprogramming languages, multiparadigm languages, numerical analysis, non-English-based languages, object-oriented class-based languages, object-oriented prototype-based languages, off-side rule languages, procedural languages, reflective languages, rule-based languages, scripting languages, stack-based languages, synchronous languages, syntax handling languages, visual languages, wirth languages, embeddable languages, and xml-based languages. Memory 504 may also be used for storing temporary variable or other intermediate information during execution of instructions to be executed by processor 502.

A computer program as discussed herein does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network. The processes and logic flows described in this specification can be performed by one or more programmable processors executing one or more computer programs to perform functions by operating on input data and generating output.

Computer system 500 further includes a data storage device 506 such as a magnetic disk or optical disk, coupled to bus 508 for storing information and instructions. Computer system 500 may be coupled via input/output module 510 to various devices (e.g., barcode reader 34 and 24). The input/output module 510 can be any input/output module. Example input/output modules 510 include data ports such as USB ports. The input/output module 510 is configured to connect to a communications module 512. Example communications modules 512 (e.g., communications module 218 and 238) include networking interface cards, such as Ethernet cards and modems. In certain aspects, the input/output module 510 is configured to connect to a plurality of devices, such as an input device 514 (e.g., input device 116 of client 110 and input device 136 of server 130) and/or an output device 516 (e.g., output device 114 and 134). Example input devices 514 include a keyboard and a pointing device, e.g., a mouse or a trackball, by which a user can provide input to the computer system 500. Other kinds of input devices 514 can be used to provide for interaction with a user as well, such as a tactile input device, visual input device, audio input device, or brain-computer interface device. For example, feedback provided to the user can be any form of sensory feedback, e.g., visual feedback, auditory feedback, or tactile feedback; and input from the user can be received in any form, including acoustic, speech, tactile, or brain wave input. Example output devices 516 include display devices, such as a LED (light emitting diode), CRT (cathode ray tube), or LCD (liquid crystal display) screen, for displaying information to the user.

According to one aspect of the present disclosure, the client 110 and server 130 can be implemented using a computer system 500 in response to processor 502 executing one or more sequences of one or more instructions contained in memory 504. Such instructions may be read into memory 504 from another machine-readable medium, such as data storage device 506. Execution of the sequences of instructions contained in main memory 504 causes processor 502 to perform the process steps described herein. One or more processors in a multi-processing arrangement may also be employed to execute the sequences of instructions contained in memory 504. In alternative aspects, hard-wired circuitry may be used in place of or in combination with software instructions to implement various aspects of the present disclosure. Thus, aspects of the present disclosure are not limited to any specific combination of hardware circuitry and software.

Various aspects of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. The communication network (e.g., network 150) can include, for example, any one or more of a personal area network (PAN), a local area network (LAN), a campus area network (CAN), a metropolitan area network (MAN), a wide area network (WAN), a broadband network (BBN), the Internet, and the like. Further, the communication network can include, but is not limited to, for example, any one or more of the following network topologies, including a bus network, a star network, a ring network, a mesh network, a star-bus network, tree or hierarchical network, or the like. The communications modules can be, for example, modems or Ethernet cards.

Computing system 500 can include clients and servers. A client and server are generally remote from each other and typically interact through a communication network. The relationship of client and server arises by virtue of computer programs running on the respective computers and having a client-server relationship to each other. Computer system 500 can be, for example, and without limitation, a desktop computer, laptop computer, or tablet computer. Computer system 500 can also be embedded in another device, for example, and without limitation, a mobile telephone, a personal digital assistant (PDA), a mobile audio player, a Global Positioning System (GPS) receiver, a video game console, and/or a television set top box.

The term "machine-readable storage medium" or "computer readable medium" as used herein refers to any medium or media that participates in providing instructions or data to processor 502 for execution. Such a medium may take many forms, including, but not limited to, non-volatile media, volatile media, and transmission media. Non-volatile media include, for example, optical disks, magnetic disks, or flash memory, such as data storage device 506. Volatile media include dynamic memory, such as memory 504. Transmission media include coaxial cables, copper wire, and fiber optics, including the wires that comprise bus 508. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, or any other medium from which a computer can read. The machine-readable storage medium can be a machine-readable storage device, a machine-readable storage substrate, a memory device, a composition of matter effecting a machine-readable propagated signal, or a combination of one or more of them.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Furthermore, to the extent that the term "include," "have," or the like is used in the description or the claims, such term is intended to be inclusive in a manner similar to the term "comprise" as "comprise" is interpreted when employed as a transitional word in a claim.

A reference to an element in the singular is not intended to mean "one and only one" unless specifically stated, but rather "one or more." The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While this specification contains many specifics, these should not be construed as limitations on the scope of what may be claimed, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the aspects described above should not be understood as requiring such separation in all aspects, and it should be understood that the described program components and systems can generally be integrated together in a single software product or packaged into multiple software products.

The subject matter of this specification has been described in terms of particular aspects, but other aspects can be implemented and are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous. Other variations are within the scope of the following claims.

These and other implementations are within the scope of the following claims.

What is claimed is:

1. A system for managing preparation of a medication for a patient, the system comprising:
   a display screen;
   a memory comprising instructions; and
   one or more processors configured to execute the instructions to:
      receive information indicative of an order for medication for a patient from an electronic data feed;
      determine a display position of an indicator of the order for the medication in a virtual queue configured to display multiple medication orders to be filled based on at least one of an estimated amount of time to prepare the medication, an estimated amount of time to deliver the medication to a delivery location, an estimated time at which the medication will be needed for administration to a patient at the delivery location, a delivery deadline for the medication, a degree of urgency for delivery of the medication, a type of the medication, or a component of the medication;
      aggregate a group of received orders into an aggregated group of orders having a same medication type or a same medication component as the medication, such that, when displayed, the display position of the indicator in the virtual queue is visually associated with another medication in the aggregated group having the same medication type or the same medication component as the medication;
      provide the virtual queue for display on the display screen with the indicator of the order for medication visually displayed at the display position in the virtual queue, in the aggregated group with an indicator of the another medication displayed in the virtual queue;
      receive an electronically obtained user verification of an electronic record that the medication was prepared with the component of the medication; and
      transmit to a remote device remote from the system, based on receiving the user verification, a notification configured to cause a display of a graphical visualization of a path associated with a delivery of the medication at the remote device,
      wherein when the medication and the other medication have the same medication component, the one or more processors is further configured to provide, for display with the virtual queue, a total amount of the component needed to prepare both the medication and the other medication.

2. The system of claim 1, wherein the electronic data feed comprises data configured for a Health Level 7 (HL7) framework.

3. The system of claim 2, wherein the data configured for a HL7 framework comprises medical device data indicating a current or previous status of a medical device.

4. The system of claim 1, wherein the one or more processors is further configured to:
   identify a delivery location for the order of medication;
   determine whether an order for another medication is ready for delivery to or near the delivery location; and
   provide a notification to a device associated with a delivery person responsible for delivering the order for the medication to delay delivery of the other medication until the order of medication has been filled.

5. The system of claim 1, wherein the system further comprises an image recording device, wherein the order for the medication comprises at least one component to be formulated into the medication, and wherein the one or more processors is further configured to:
   capture, using the image recording device, an image, video, or barcode information identifying the component used to formulate the medication;
   store the captured image, video, or barcode information in a storage device, in association with a record of the preparation of the medication; and
   receive a user verification of the captured image, video, or barcode before transmitting the notification regarding a delivery of the medication.

6. The system of claim 1, wherein the one or more processors is further configured to:
   determine whether the order for medication for the patient can be filled with a returned medication;
   when the determination indicates the order can be filled with a returned medication, provide a notification to fill the order with the returned medication; and
   when the determination indicates a returned medication is not available to fill the order, provide a notification to fill the order by preparing the medication.

7. The system of claim 6, wherein the one or more processors is further configured to determine whether the order can be filled with an available prepared medication, and wherein the one or more processors is configured to determine whether the order for medication for the patient can be filled with a returned medication when the determination whether the order can be filled with an available prepared medication indicates a prepared medication is not available to fill the order.

8. The system of claim 6, wherein when the determination indicates that the order for the medication for the patient can be filled with a returned medication, the one or more processors is further configured to provide, for display, an identification of a pickup location at which the returned medication can be retrieved.

9. The system of claim 8, wherein the identification of the pickup location is provided to the remote device with the notification, and wherein the one or more processors is further configured to generate the path based on the pickup location and a delivery location of at least one other medication, wherein the graphical visualization of the path comprises a path by which a delivery person can retrieve the returned medication while delivering the at least one other medication overlaid on a graphically displayed map.

10. The system of claim 6,
wherein the determination whether the order for the medication for the patient can be filled with a returned medication is based on at least one of an expiration time of the returned medication, an estimated amount of time for delivering the returned medication to the patient, an estimated time at which the returned medication will be administered to the patient, or a delivery deadline for the order for the medication for the patient, and
wherein the expiration time of the returned medication is determined based on at least one of a sterility of the returned medication or a stability of the returned medication.

11. A method for managing preparation of a medication for a patient, the method comprising:
receiving information indicative of an order for medication for a patient from an electronic data feed;
determining, by one or more computing devices, a display position of an indicator of the order for the medication in a virtual queue configured to display multiple medication orders to be filled based on at least one of an estimated amount of time to prepare the medication, an estimated amount of time to deliver the medication to a delivery location, an estimated time at which the medication will be needed for administration to a patient at the delivery location, a delivery deadline for the medication, a degree of urgency for delivery of the medication, a type of the medication, or a component of the medication;
aggregating a group of the multiple medication orders to include the medication and another medication having a same medication type or a same medication component as the medication;
providing, using the one or more computing devices, the virtual queue for display on a display screen with indicators corresponding to the aggregated group of orders visually displayed in the virtual queue such that the indicator of the order of the medication is provided for display grouped with an indicator of the another medication in the virtual queue;
receiving, by the one or more computing devices, an electronically obtained user verification of an electronic record that the medication was prepared with the component of the medication; and
transmitting, by the one or more computing devices, to a remote device, remote from the one or more computing devices, based on receiving the user verification, a notification configured to cause a display of a graphical visualization of a path associated with a delivery of the medication at the remote device,
wherein when the medication and the other medication have the same medication component, the method further comprises providing, for display with the virtual queue, a total amount of the component needed to prepare both the medication and the other medication.

12. The method of claim 11, wherein the electronic data feed comprises data configured for a Health Level 7 (HL7) framework.

13. The method of claim 12, wherein the data configured for a HL7 framework comprises medical device data indicating a current or previous status of a medical device.

14. The method of claim 11, further comprising:
identifying a delivery location for the order of medication;
determining whether an order for another medication is ready for delivery to or near the delivery location; and
providing a notification to a device associated with a delivery person responsible for delivering the order for the medication to delay delivery of the other medication until the order of medication has been filled.

15. The method of claim 11, wherein the order for the medication comprises at least one component to be formulated into the medication, and the method further comprising:
capturing, using an image recording device, an image, video, or barcode information identifying the component used to formulate the medication;
storing the captured image, video, or barcode information in a storage device, in association with a record of the preparation of the medication; and
receiving a user verification of the captured image, video, or barcode before transmitting the notification regarding a delivery of the medication.

16. The method of claim 11, further comprising:
determining whether the order for medication for the patient can be filled with a returned medication;
when the determination indicates the order can be filled with a returned medication, providing a notification to fill the order with the returned medication; and
when the determination indicates a returned medication is not available to fill the order, providing a notification to fill the order by preparing the medication.

17. The method of claim 16, further comprising determining whether the order can be filled with an available prepared medication, and wherein the determining whether the order for medication for the patient can be filled with a returned medication is in response to the determination whether the order can be filled with an available prepared medication indicating a prepared medication is not available to fill the order.

18. The method of claim 16, wherein when the determination indicates that the order for the medication for the patient can be filled with a returned medication, the method further comprises providing, for display, an identification of a pickup location at which the returned medication can be retrieved.

19. The method of claim 18, wherein the identification of the pickup location is provided to the remote device with the notification, and wherein the method further comprises generating the path based on the pickup location and a delivery location of at least one other medication, wherein the graphical visualization of the path comprises a path by which a delivery person can retrieve the returned medication while delivering the at least one other medication overlaid on a graphically displayed map.

20. The method of claim 16,
wherein the determination whether the order for the medication for the patient can be filled with a returned medication is based on at least one of an expiration time of the returned medication, an estimated amount of time for delivering the returned medication to the patient, an estimated time at which the returned medication will be administered to the patient, or a delivery deadline for the order for the medication for the patient, and wherein the expiration time of the returned medication is determined based on at least one of a sterility of the returned medication or a stability of the returned medication.

21. A non-transitory machine-readable storage medium comprising machine-readable instructions for causing a processor to execute a method for managing preparation of a medication for a patient, the method comprising:

receiving information indicative of a first order for a first medication for a patient from an electronic data feed, the order comprising a medication component to be formulated into the first medication;

determining a display position of the first order in a virtual queue configured to display multiple medication orders to be filled based on at least one of an estimated amount of time to prepare the first medication, an estimated amount of time to deliver the first medication to a delivery location, an estimated time at which the first medication will be needed for administration to a patient at the delivery location, a delivery deadline for the first medication, a degree of urgency for delivery of the first medication, a type of the first medication, or a component of the first medication;

aggregating, within the virtual queue, the first order and one or more received orders into an aggregated group of orders having the same medication component as the first medication, the aggregated group of orders comprising a second order for a second medication having a display position associated with a display position of the first order;

providing the virtual queue, including the aggregated group of orders, for display on a display screen;

capturing, using an image recording device, an image, video, or barcode information identifying the medication component formulate the medication;

storing, as verification of an electronic record that the first medication was prepared for the first order with the component of the medication, the captured image, video, or barcode information in a storage device, in association with a record of the preparation of the medication; and transmitting, by the one or more computing devices, after storing the verification, to a remote device, remote from the processor, based on receiving the user verification, a notification configured to cause a display of a graphical visualization of a path associated with a delivery of the medication at the remote device.

* * * * *